United States Patent [19]

Sato et al.

[11] Patent Number: 4,566,460

[45] Date of Patent: Jan. 28, 1986

[54] MEASURING METHOD AND APPARATUS FOR NON-LINEAR PARAMETER OF ACOUSTIC MEDIUM AND ITS APPLICATION

[75] Inventors: Takuso Sato, Tokyo; Nobuyuki Ichida, Machida; Hirohide Miwa, Kawasaki, all of Japan

[73] Assignee: Fujitsu Limited, Kawasaki, Japan

[21] Appl. No.: 587,522

[22] Filed: Mar. 8, 1984

[30] Foreign Application Priority Data

Mar. 10, 1983 [JP] Japan .................................. 58-39907

[51] Int. Cl.⁴ ...................... A61B 10/00; G01N 29/00
[52] U.S. Cl. .................................... 128/660; 128/736; 374/117; 73/602
[58] Field of Search ............................... 128/660–663; 73/597, 602, 625–626; 374/117

[56] References Cited

U.S. PATENT DOCUMENTS 4,431,008  2/1984  Warner et al. ...................... 128/660

FOREIGN PATENT DOCUMENTS 59-55245  3/1984  Japan .

OTHER PUBLICATIONS

Papers by Ichida et al., pp. 59–67, 1982.
"Real-Time Nonlinear Parameter Tomography Using Impulsive Pumping Waves", IEEE Transactions on Sonics and Ultrasonics, vol. SU-31, No. 6, Nov. 1984, pp. 635–641.
"Imaging the Nonlinear Ultrasonic Parameter of a Medium", Ultrasonic Imaging 5, 1983, pp. 295–299.
"Prediction of Nonlinear Acoustic Effects at Biomedical Frequencies and Intensities", T. G. Muir et al., *Ultrasound in Med. and Biol.*, pp. 345–357, Great Britain, 1980.

*Primary Examiner*—Kyle L. Howell
*Assistant Examiner*—Francis J. Jaworski
*Attorney, Agent, or Firm*—Staas & Halsey

[57] ABSTRACT

A measuring method and apparatus for measuring a non-linear parameter of an acoustic medium or its distribution, and the application of the parameter to the measurement of internal temperature of a sample noninvasively. A continuous wave ultrasonic probing beam is radiated through the sample, and a pumping wave which is an ultrasonic pulse is superposed on the probing beam. A phase change in the probing beam caused by the pumping wave is detected. From this phase change the non-linear parameter (B/A) is obtained. The invention projects two methods. The first method provides the pumping wave in a direction intersecting the probing beam. The second method projects the pumping wave in a direction along the probing beam in counter direction. From the information concerning the variation of measured value of (B/A), the inner temperature of the sample is obtained. The invention makes it possible to measure the non-linear parameter or temperature which was impossible in the prior art.

29 Claims, 36 Drawing Figures

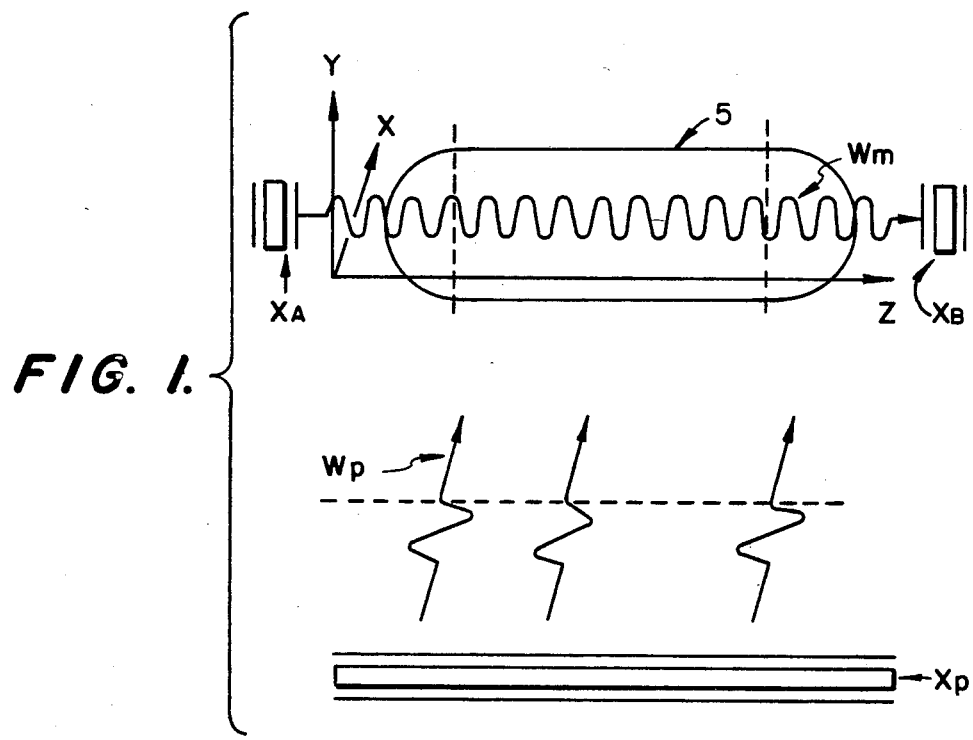

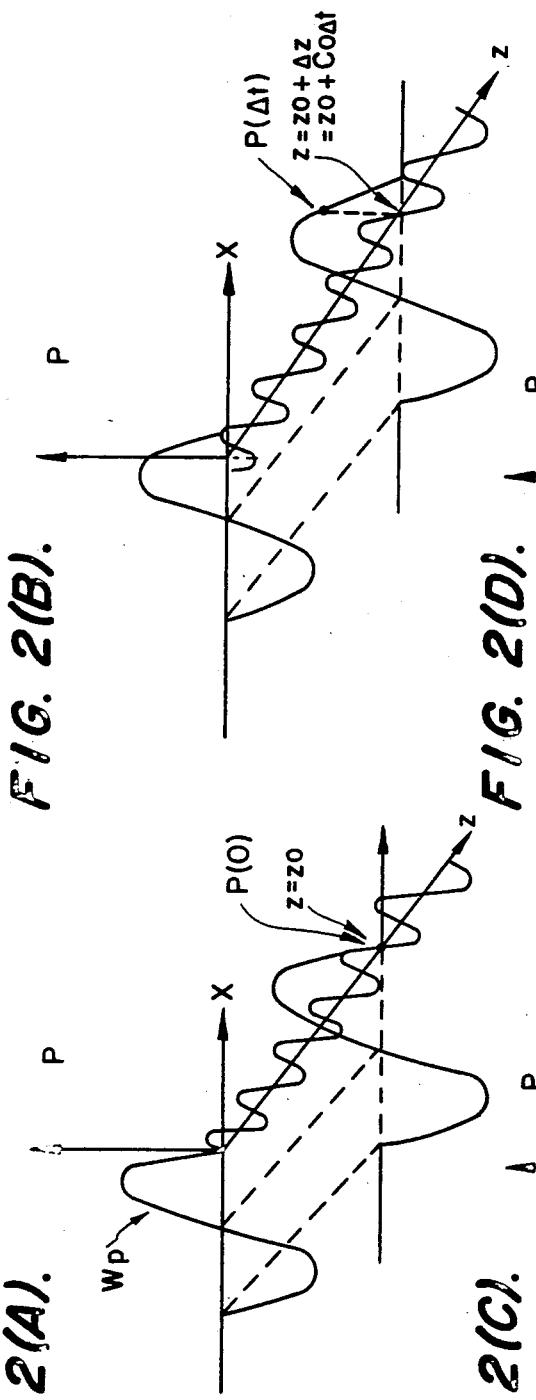
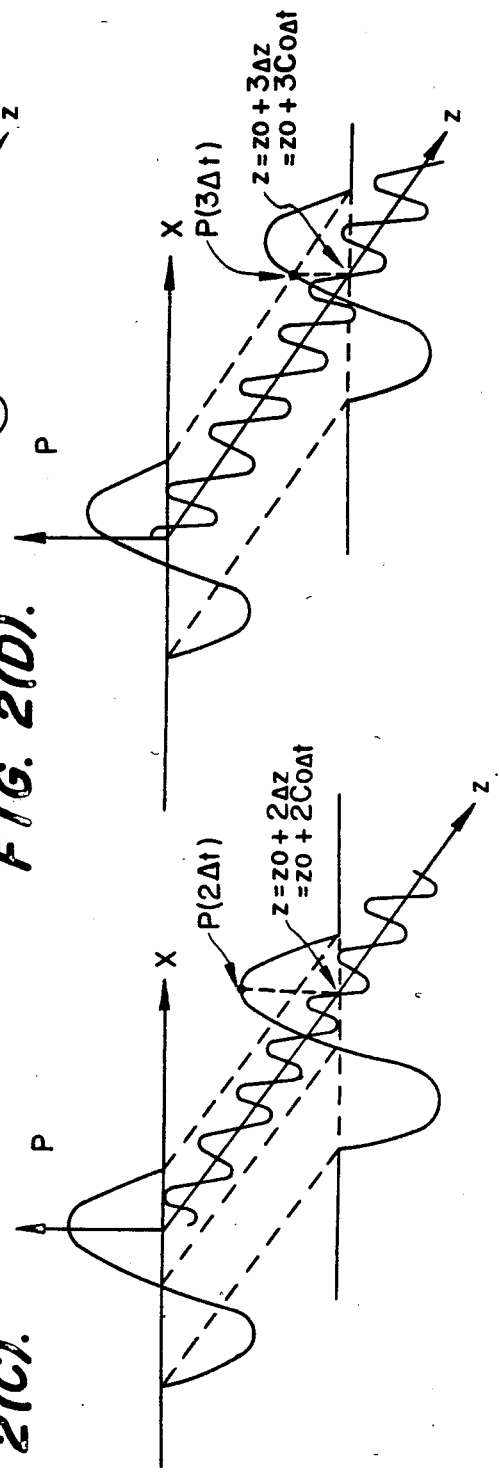
FIG. 2(A).  FIG. 2(B).
FIG. 2(C).  FIG. 2(D).

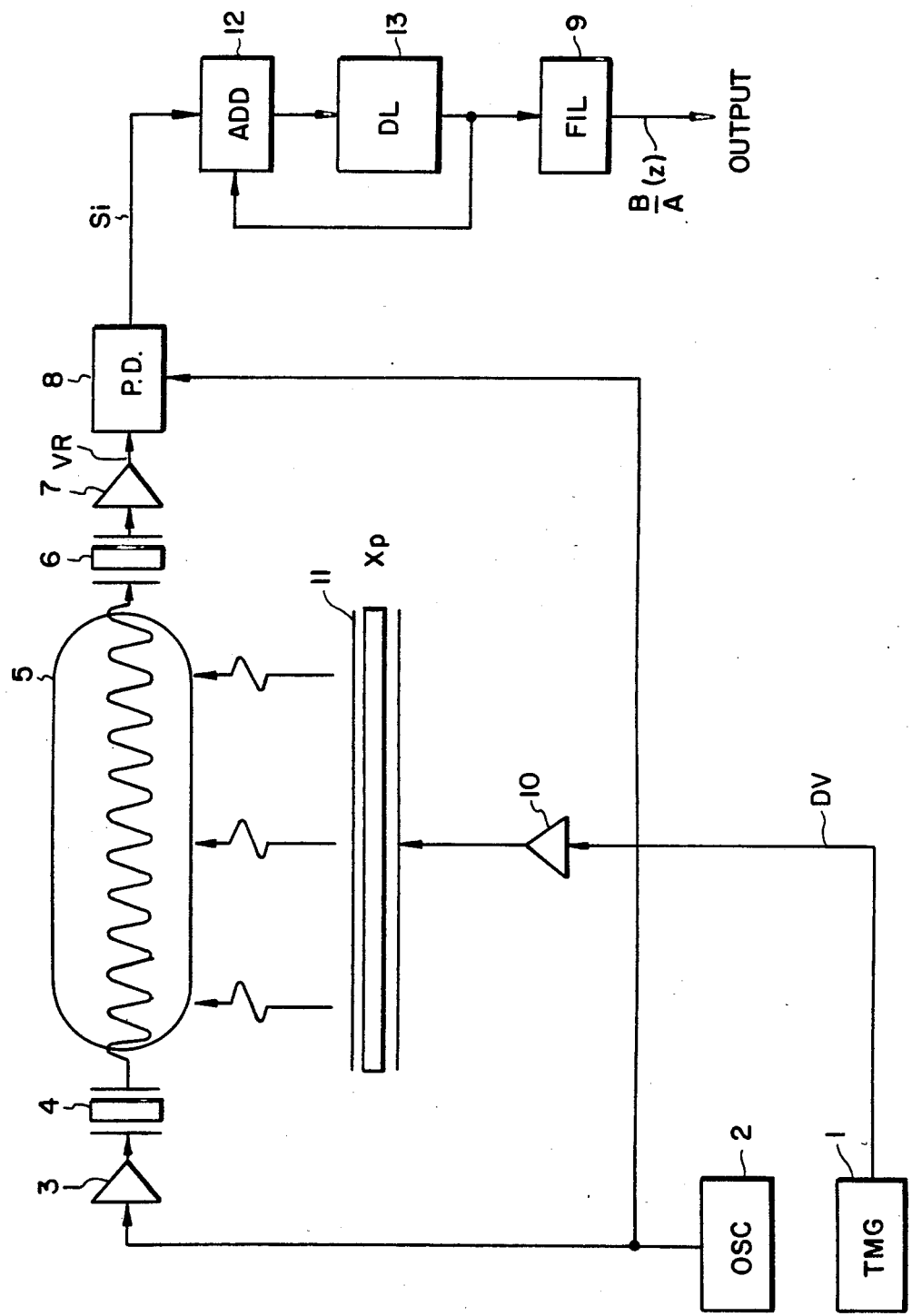

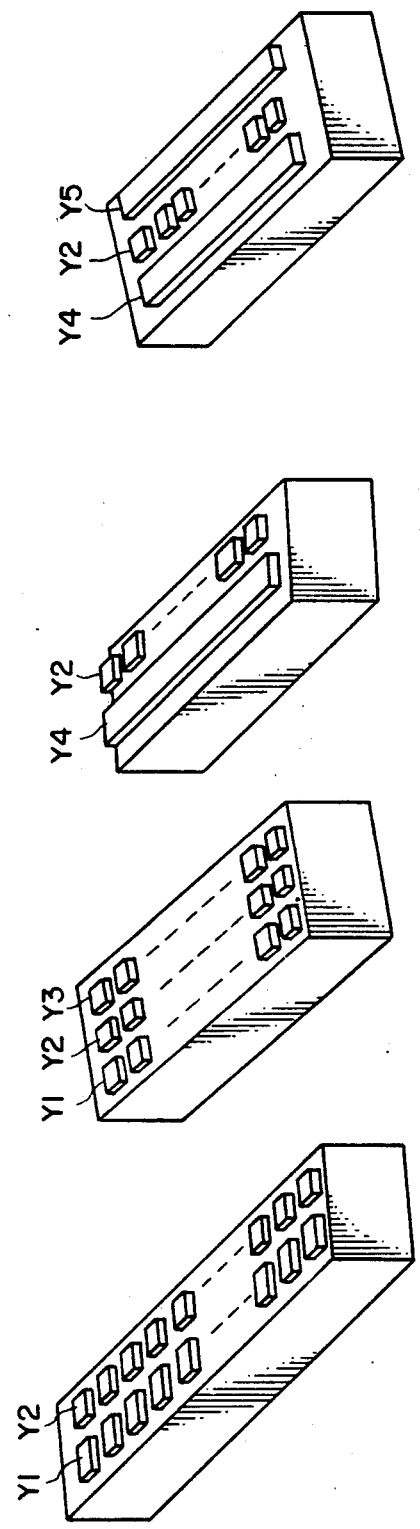

PROBING WAVE FREQUENCY

MEASURING METHOD AND APPARATUS FOR NON-LINEAR PARAMETER OF ACOUSTIC MEDIUM AND ITS APPLICATION

BACKGROUND OF THE INVENTION

1. Field of the Invention

The present invention relates to a measuring method and apparatus for measuring a non-linear parameter and/or its distribution in an acoustic medium. It also relates to the application of the method to measurements such as temperature measurement of human tissue for an ultrasonic diagnosis, hyperthermia, etc. The measuring apparatus of the present invention especially relates to a device for measuring a non-linear parameter of an acoustic medium such as biomedical tissue, measuring the space distribution of the non-linear parameter of the acoustic medium and displaying an image of the space distribution on a display unit. The measuring method and apparatus of the present invention is useful in many applications and primarily intends to provide special apparatus to measure the temperature of internal tissue noninvasively.

2. Discussion of the Prior Art

Usually, an ultrasonic apparatus such as an ultrasonic tomograph, is designed while assuming a pressure independent sound speed. In the first approximation, sound speed is regarded as a pressure independent constant and the density of the acoustic medium is also regarded as pressure independent for a liquid and a solid medium like tissue. However, more accurately, sound speed relates to the density (it is called dynamic density) at each infinitesimal portion of the acoustic medium through which the sound wave propagates, and because a sound wave is a compressional wave, the density of each part of the acoustic medium is varied by an increase in sound pressure.

The relationship between sound speed and density of a medium through which the sound wave propagates can be expressed as $$\Delta p = A \, \Delta \rho + B \frac{\Delta \rho^2}{2} + \cdots.$$

This results in a nonlinearity relationship between sound speed and pressure expressed as $$C = C_0 + \frac{1}{2 \rho_0 C_0} (B/A) \cdot \Delta p, \quad (1)$$

where, $\Delta \rho$: dynamic density change caused by $\Delta p$;

$\Delta P$: dynamic sound pressure, that is a variation of the pressure caused by the sound wave propagating in the acoustic medium;

C: sound speed resulting under dynamic sound pressure $\Delta p$;

$C_0$: sound speed (phase velocity) resulting under static pressure, that is sound speed of infinitesimaly small amplitude propagating through the medium;

$\rho_0$: static density, density of the acoustic medium under static pressure; and B/A: a non-linear parameter of the acoustic medium.

Equation (1) is applicable only under a second order approximation where the higher order terms have been neglected or eliminated from the equation. If the second order term is neglected, equation (1) keeps only first order term resulting linear acoustic equation; that is, sound speed is pressure independent as mentioned above as a "first approximation". More details about the non-linear acoustics are explained, for example, by T. G. MUIR, E. L. CARSTENSEN in 1979 (Prediction of Nonlinear Acoustic Effects at Biomedical Frequencies and Intensities; Ultrasound in Med. & Biol., Vol.6; Pergamon Press Ltd.).

Recently, the non-linear parameter B/A has become worthy of notice in the field of ultrasonic technology, because it includes novel information such as: the structure, the coupling state, the visco-elasticity, and the temperature of biomedical tissue; the chemical state of a body fluid; the metabolic activity; and so on. However, the quantity B/A is so small that it has been difficult to put it into practical use. To overcome this difficulty, an equivalent non-linear parameter $(B/A)_e$ was introduced by N. Ichida, T. Sato, O. Ikeda and M. Linzer (Ultrasonic Imaging of the Non-linear Parameter of Tissue Using Scanned Low Frequency Pumping Waves and High Frequency Probe Waves) at the 7th International Symposium On Ultrasonic Imaging And Tissue Characterization, held on Jan. 6–9, 1982, sponsored by NBS, and in Japanese Patent Application No. TOKUGAN-SHO 57-167036, in 1982 (Ultrasonic Diagnostic Processing System) by the inventors. This new measuring method introduced a second sound wave (pumping wave) into the acoustic medium to be measured, to detect the second order term in equation (1). Therefore, two kinds of sound waves are superimposed in the acoustic medium. One is a "probing wave" to measure the non-linear parameter of the medium, and the other is "pumping wave" to generate the $\Delta p$. The amplitude of the pumping wave is made sufficiently higher than the probing wave, so that the non-linear parameter is enhanced to make it easy to measure. The non-linear parameter measured in this way is called "equivalent non-linear parameter $(B/A)_e$", and equation (1) is modified as follows $$C = C_0 + \frac{1}{2 \rho_0 C_0} \left( \frac{B}{A} \right)_e \cdot P, \quad (2)$$

where, $(B/A)_e$ is an equivalent non-linear parameter;

P is sound pressure of the pumping wave; and

C, $C_0$, and $\rho_0$ are the same as defined in equation (1), respectively.

At first a measuring method of the parameter $(B/A)_e$ by the prior Patent Application will be described briefly. A pumping wave consists of a continuous wave (CW), whose wave length is varied. A probing wave is also CW and is applied to the medium by a pair of ultrasonic transducers; one of which transmits the probing wave and the other receives the probing wave. The phase of the transmitted probing wave is modulated by the pumping wave as it crosses the probing wave beam through the medium. The parameter $(B/A)_e$ along the medium can be obtained by a Fourier transformation of the phase deviations of the received probing wave caused by the pumping wave corresponding to the various wavelengths of the pumping wave.

The above-mentioned prior art method of measuring the parameter $(B/A)_e$, however, had the following problems in attaining a good result rapidly.

(1) The frequency of the pumping wave had to be varied very widely, however, it is not normal for a transducer to have the necessary frequency band-width capable of transmitting the pumping wave effectively.

(2) The pumping wave had to be varied though many frequencies to get a high degree of resolution, so the apparatus received plenty of time to accumulate the data, and to perform the Fourier transformation.

SUMMARY OF THE INVENTION

The object of the present invention, therefore, is to provide a means to measure an "equivalent" non-linear parameter $(B/A)_e$ of the acoustic medium effectively and rapidly.

Another object of the present invention is to provide a device to measure a conventionally defined (not equivalent) non-linear parameter (B/A) of the acoustic medium with a more practical convenience of application.

A further object of the present invention is to provide two/three dimensional image(s) of the acoustic non-linear parameter of the acoustic equivalent non-linear parameter.

Still another object of the present invention is to providing a device to measure the temperature of internal tissue noninvasively by applying the above-mentioned devices.

For the measurement of the equivalent non-linear parameter $(B/A)_e$ or the non-linear parameter (B/A) the present invention provides two methods.

The first method measures the parameter $(B/A)_e$ by applying a pulsed pumping wave instead of prior art continuous pumping wave, and the pulsed pumping wave propagates and intersects the probing beam. Applying the pulsed pumping wave is equivalent to using many frequency for the pumping wave, and it is not necessary to vary the CW frequency and waste time. This method is performed by using a pair of transducers for the probing wave, and a single transducer for the pumping wave. The former are arranged face to face with each other across the acoustic medium to be measured, transmitting and receiving the probing wave (probing beam). The latter produces a wide beam of sound covering the measured region, and supplies pumping sound pressure to the medium uniformly and simultaneously.

The second method measures the parameter (B/A) by providing a pumping beam in which the pulsed pumping wave propagates in a direction counter to the probing wave propagation direction. This method is performed by using a pair of transducers for the probing wave, and the single pumping transducer is located near the receiving probing transducer. An array type transducer is applicable for the above transducer.

A space distribution image of the parameter $(B/A)_e$ or (B/A) can be obtained by using the probing beam which scans the acoustic medium in one or two dimensions.

A device which measures the internal temperature of an acoustic medium can be provided based on a referential data for the parameter $(B/A)_e$ or (B/A) measured previously as a function of temperature in the acoustic medium such as biomedical tissue. Because the parameter $(B/A)_e$ or (B/A) is sensitive to temperature. An image of the internal medium temperature distribution can be obtained by the intermediation of $(B/A)_e$ or (B/A) along the probing beam, in two or three dimensions in the same way as described above.

BRIEF DESCRIPTION OF THE DRAWINGS

FIG. 1 is a diagram illustrating the principle of the first measuring method of the present invention having a pumping wave which propagates perpendicular to a probing beam.

FIG. 2, including FIG. 2(A)-2(D), is a perspective view illustrating a phase relation between the probing wave and the pumping wave of the measuring method of FIG. 1.

FIG. 3 is a block diagram of a measuring apparatus of the present invention having a pumping wave which propagates perpendicular to the probing beam.

FIG. 7 is another block diagram of a measuring apparatus embodying the present invention which improves the S/N ratio of the apparatus.

FIGS. 15(A)-15(D) are perspective diagrams of various array transducer constructions for the second measuring method of the present invention.

FIG. 16(A) shows an array construction having one array in which a probing transducer element and a pumping element are arranged alternately; and FIG. 16(B) shows an array construction having one array in which probing transducer elements are arranged in every third place.

FIG. 17 is a graph of the frequency characteristics of a transducer which functions as both the probing and pumping transducer, for the second measuring method of the present invention, where

DESCRIPTION OF THE PREFERRED EMBODIMENTS

Figure 4:
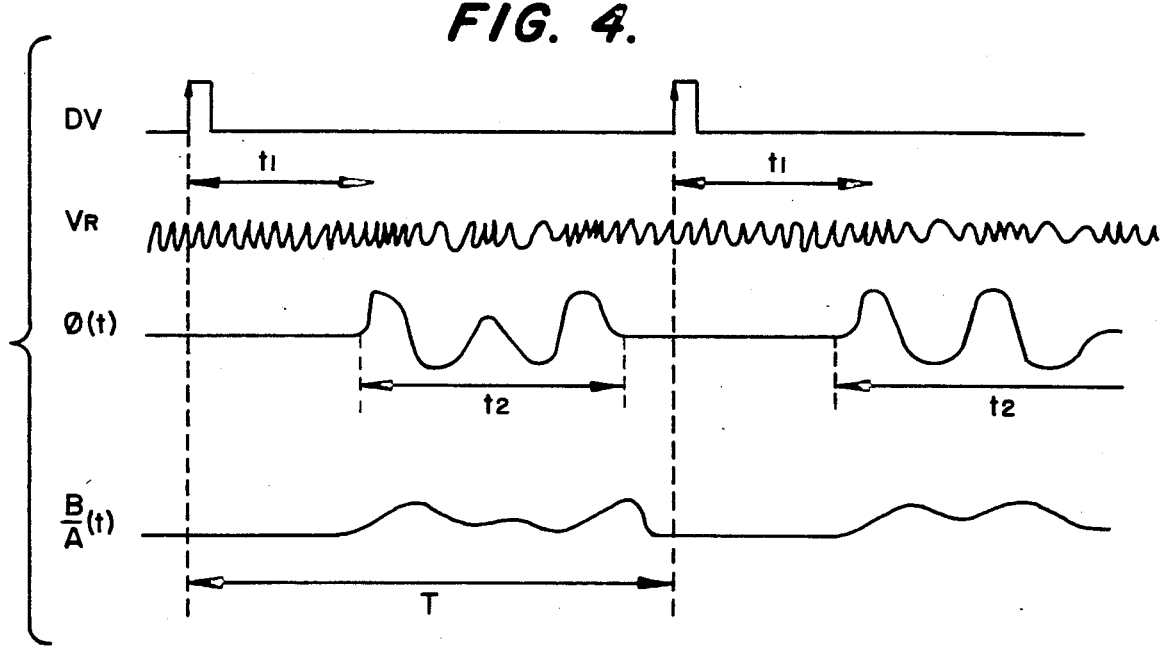
FIG. 4 shows the waveforms of the signals at the points indicated in FIG. 3.

Further details and advantages of the present invention will be understood with respect to preferred embodiments discussed herein and drawings attached hereto and made a part hereof.

As previously noted, the present invention involves an improved measuring method and apparatus for measuring the equivalent non-linear parameter and the non-linear parameter of the acoustic medium using the pulse pumping wave.

FIG. 1 is a diagram illustrating the first measuring method of the present invention. Usually, measurement is carried on in water, though it is not shown in the figure, by immersing the medium to be measured and the instruments in the water. The method uses a pumping wave $W_p$ which is generated pulsively, and has a planar wave front, which propagates in the medium to be measured perpendicularly to the probing wave propagation path. In FIG. 1, 5 is a medium placed in water between the transducers $X_A$ and $X_B$ which form a probing beam in the direction of the Z axis. $X_A$ transmits a beam-shaped probing wave $W_m$ into the medium 5, $X_B$ receives $W_m$ which is modulated by a sound pressure of pumping wave $W_p$, while $W_m$ passes through the medium 5. $W_p$ is radiated by a pumping wave transducer $X_p$ in the direction of the X axis. X, Y and Z are the axes of a rectangular coordinate respectively.

Under the above conditions, the equivalent non-linear parameter $(B/A)_e$ is calculated from equation (2) as $$\left(\frac{B}{A}\right)_e = 2\rho_0 C_0 \left(\frac{\delta C_i}{\delta P_j}\right)_s, \tag{3}$$

When the medium is not uniform, the parameter $(B/A)_e$ varies at each point corresponding the heterogeneity of the medium at that point. The suffix i and j indicate directions which are perpendicular to each other, and suffix s means "under an isoentropic condition", that is under a quasistatic process, or in a process of adiabatic compression or expansion. A conventionally defined non-linear parameter B/A in an acoustic field is determined when $i=j$, by $$\frac{B}{A} = 2\rho_0 C_0 \left(\frac{\delta C_i}{\delta P_i}\right)_s. \tag{4}$$

If the medium is isotropic, the following relationship can be obtained, $$\left(\frac{B}{A}\right)_e = \left(1 + \frac{2\nu - 1}{1 - \nu}\right) \frac{B}{A}, \tag{5}$$

where, $\nu$ is Poison's ratio whose value is about 0.5 for liquid or biomedical tissue, so it can be said that $(B/A)_e$ is almost equal to B/A if the acoustic medium is assumed to be something such as biomedical tissue. Therefore, $\Delta C$ a variation of sound speed due to the pressure P of the pumping wave can be determined by $$\Delta C = \frac{1}{2\rho_0 C_0} \left(\frac{B}{A}\right)_e \cdot P. \tag{6}$$

In FIG. 1, for simplicity, it can be assumed that sound pressure of $W_m$ is sufficiently lower than sound pressure of $W_p$ so that P of equation (2) or (6) only depends on the sound pressure of $W_p$.

In a period when the pumping wave $W_p$ (which is a pulsed wave) intersects the probing beam, the sound speed change $\Delta C$ of probing wave $W_m$ occurs. The value of $\Delta C$ varies at each position on the Z axis, so equation (6) can be expressed by $$\Delta C(z) = \frac{1}{2\rho_0 C_0} \left(\frac{B}{A}\right)_e (z) \cdot P, \tag{7}$$

where, z is a coordinate of the Z axis. Equation (7) indicates that the waveform of $W_m$ at each position along the Z axis suffers a phase change proportional to $\Delta C(z)$. Then, $(B/A)_e(z)$ can be estimated from phase information included in the output signal of the receiving transducer $X_B$. The value of P in equation (7) can be measured previously in an equivalent liquid. Detail concerning the above considerations are as follows.

FIG. 2 shows diagrammatically perspective views of the probing wave $W_m$ which is affected by sound pressure of the pumping wave $W_p$ while $W_m$ propagates through the acoustic medium. The medium is assumed to be homogeneous. The sound of $W_p$ is a function of time, therefore, P can be described as P(t), where t is time. At $z=z_0$ and when $t=0$, $W_m$ is affected by pressure P(O) (see FIG. 2 (A)). After a short time period both the probing wave and pumping wave shift their position, so that at $t=\Delta t$, $z=z_0+\Delta z=z_0+C_0\Delta t$ and the sound pressure becomes $P(t+\Delta t)$ (see FIG. 2(B)). In the same manner, $W_m$ is affected by sound pressure P such as shown in FIG. 2(C) when $t=2\Delta t$, FIG. 2(D) when $t=3\Delta t$, respectively.

From the above explanation, it can be said generally that a probing wave $W_m$ positioned at $z_0$ at $t=0$, will receive following pressure change (that is a change of sound velocity) at z $$\Delta C(z) = \frac{1}{2\rho_0 C_0} \left(\frac{B}{A}\right)_e (z) \cdot P(\Delta t) \quad (8)$$

$$= \frac{1}{2\rho_0 C_0} \left(\frac{B}{A}\right)_e (z) \cdot P\left(\frac{z-z_0}{C_0}\right),$$

however, value of $\Delta C(z)$ is less than $C_0$, $\Delta t$ is a time interval in which $W_m$ propagates from $z_0$ to $z$ and is given by the following approximate equation $$\Delta t = \frac{z-z_0}{C_0}. \quad (9)$$

Therefore, when probing wave $W_m$ propagates from $z_0$ to $z$, a phase change of $W_m$ can be expressed as $$\Delta \psi(z)_{z_0} = K \cdot \left(\frac{B}{A}\right)_e (z) \cdot P\left(\frac{z-z_0}{C_0}\right), \quad (10)$$

where,
K: proportional constant, and
$\Delta \psi_{z_0}(z)$: phase change of $W_m$ as a function of z.
The total of the phase change of $W_m$ while the probing wave propagates in the acoustic medium from transmitting transducer $X_A$ to receiving transducer $X_B$ is given by $$\phi(z_0) = \int_{\infty}^{\infty} \Delta \psi_z(z) dz \quad (11)$$

$$= K \int_{\infty}^{\infty} \left(\frac{B}{A}\right)_e (z) \cdot P\left(\frac{z-z_0}{C_0}\right) dz.$$

substituting following function g into the equation (11), $$g(z_0 - z) = P\left(\frac{z-z_0}{C}\right), \quad (12)$$

the following equation is obtained, $$\phi(z_0) = K \int_{\infty}^{\infty} \left(\frac{B}{A}\right)_e (z) \cdot g(z_0 - z) dz \quad (13)$$

$$= K \left\{ \left(\frac{B}{A}\right)_e (z) * g(z) \right\}.$$

Equation (13) is so-called convolution integral. If Fourier transformation is applied to equation (13), following equation can be obtained.

$$\Psi(\omega) = K \cdot \left(\frac{B}{A}\right)_e (\omega) \cdot G(\omega), \quad (14)$$

where; $\Psi(\omega)$, $(B/A)_e(\omega)$, $G(\omega)$ are respectively the Fourier transform of $\phi(z)$, $(B/A)_e(z)$, and $g(z)$; and a variable $\omega$ is a space frequency along the coordinate z.

From equation (14), following relationships are obtained, $$\left(\frac{B}{A}\right)_e (\omega) = \frac{1}{K} \frac{1}{G(\omega)} \Phi(\omega), \quad (15)$$

$$\left(\frac{B}{A}\right)_e (z) = \frac{1}{K} F^{-1} \left\{ \frac{1}{G(\omega)} \Phi(\omega) \right\}. \quad (16)$$

where $F^{-1}$ is the inverse Fourier transformation. From these equations, $(B/A)_e(z)$ can be obtained.

Equation (15) shows that $(B/A)_e$ can be obtained by filtering $\Phi(\omega)$ using a filter having frequency characteristics such as $1/(KG(\omega))$ which is the inverse characteristics of the pumping wave frequency characteristics. Therefore, the inverse Fourier transformation like equation (16) is not necessary to obtain $(B/A)_e(z)$. It can be obtained simply by applying the above filter. $G(\omega)$ in equation (15) or (16) can be obtained from $P(t)$ in equation (12).

The space distribution of the non-linear parameter $B/A(z)$ obtained by the above means can be displayed as an image, namely the image of the space distribution of $B/A(z)$. FIG. 3 is a block diagram of an apparatus for realizing this image.

In FIG. 3, reference numeral 1 designates a timing controller which controls the emission of the pumping wave $W_p$, 2 is an oscillator for the probing wave $W_m$, 3 is a driver to drive a transducer $X_A$, 4 is a transducer $X_A$ which transmits a probing wave $W_m$, 5 is an acoustic medium to be measured, 6 is a transducer $X_B$ which receives $W_m$ modulated by $W_p$, 7 is a receiving amplifier, 8 is a phase detector, 9 is a filter whose characteristics are defined by $(1/K)(1/G(\omega))$ in equation (15), 10 is a driver for the pumping wave $W_p$, and 11 is a transducer $X_p$ which radiates pumping wave $W_p$. A distance from $X_p$ to the probing beam is shown by $x_1$, and $z_2$ is a range of actual measurement in the medium 5.

FIG. 4 shows some waveforms of signals at several points in the circuit of FIG. 3. The same reference symbols are used as in corresponding parts of FIG. 3. Symbol DV is a driving pulse for the pumping transducer $X_p$, $V_R$ is an output signal of receiving amplifier 7, $\phi(t)$ is an output signal of phase detector 8, and $(B/A)(t)$ is an output signal of filter 9. In FIG. 4, $t_1$ is a sum of two time intervals $(x_1/C_0)$ and $(z_1/C_0)$. The former is a time interval between the moment the pumping wave $W_p$ is emitted and the moment $W_p$ arrives at the probing wave $W_m$, and the latter is a time interval between the moment $W_m$ is modulated by $W_p$ and the moment the front edge of the modulated part of $W_m$ is received by the transducer $X_B$. The received signal of probing wave $W_m$ begins to be phase modulated after passing the time interval $t_1$ from the moment $W_p$ had been transmitted and produces a phase modulated output $V_R$ during a time duration of $t_2$ which is the time interval during which the modulated $W_m$ passes through the length $z_2$, so it can be expressed as $t_2 = z_2/C_0$.

Phase detector 8 detects a phase shift of the received signal $V_R$ by comparing it with a phase of an output signal of oscillator 2 which produces a reference signal, and provides an output $\phi(t)$ as a function of time. However (t) can be considered as a function of position z, as mentioned before with respect to equation (9), since there is a linear relation between t and z. This output signal is filtered by filter 9, and the equivalent non-linear parameter $(B/A)_e$ can be obtained as a function of time, $(B/A)_e(t)$, that is a function of z, $(B/A)_e(z)$.

As disclosed above, by applying the measuring method of the present invention which uses a pulsed pumping wave, the space distribution of the equivalent non-linear parameter $(B/A)_e(z)$ can be rapidly measured by a simple construction an apparatus without providing various CW pumping waves and a complex Fourier transformation.

The following consideration may be helpful for the understanding of the above and for following description. Since, the pulse of the pumping wave will pass through the Z axis in an instant, because it propagates in orthogonal direction to the Z axis. At that instant, the probing wave (that is a continuous wave) is propagating in a queue (beam) on the Z axis. At the instant when the pumping wave passes over the probing wave, each portion of the probing wave will be affected by the pumping wave, and each portion of the probing wave will be phase shifted corresponding to $(B/A)_e$ at its respective point. The wave train of probing wave is stamped with the phase the value of $(B/A)_e$ at each point by the pumping pulse. Therefore, the pumping pulse may be called as stamping pulse. After the wave train is stamped, the queue (beam) of the probing wave successively reaches the receiving transducer. So, the time sequence of the phase change of the probing wave is the information regarding the distribution of $(B/A)_e$ along the Z axis.

The output signal $\phi(t)$ of phase detector 8 is described on a time axis in FIG. 4, however the phase shift of each time corresponds to the phase shift of the probing wave affected by the pumping wave at each point on the Z axis.

Therefore, if $V_R$ in FIG. 4 is obtained, it contains the information regarding $(B/A)_e$ on the Z axis. The phase of $V_R$ must have some relationship to $(B/A)_e$. The filter which extracts $(B/A)_e$ from the wave train is what is designated by reference numeral 9 in FIG. 3. If the data comes out successively from filter 9 and is plotted successively along Z direction, it shows the profile of $(B/A)_e$ along the Z axis.

In the above explanation, the pumping wave is assumed to be a plane wave, however, the plane wave is hard to realize in a practical apparatus because if a perfect plane wave is to be realized, an aperture of a pumping wave transducer should be a plane spreading infinitely. Therefore, in the actual apparatus of the present invention, a part of a spherical wave having a large radius of curvature is used as a pumping wave, thus assuming that it approximates a plane wave. It is practical to do this when considering the power needed for the generation of the pumping wave. However, in this case, the energy of the wave tends to decrease at the edge of the pumping wave. Therefore, the influence caused by a spherical wave must be compensated.

In this case, the sound pressure of the pumping wave is not only a function of t but also of position z. Therefore, the deviation of the actual pumping wave from an ideal plane wave must be compensated for, and this compensation can be performed as follows.

FIG. 5 shows schematically the above-mentioned situations. FIG. 5(A) shows the distribution of the sound pressure of the pumping wave at a time $t=0$, when the wave front of a spherical pumping has arrived at the z axis (position of the probing beam). Two broken lines indicate the front and rear edge of the pumping wave pulse respectively, propagating in the X direction.

Figure 5A:
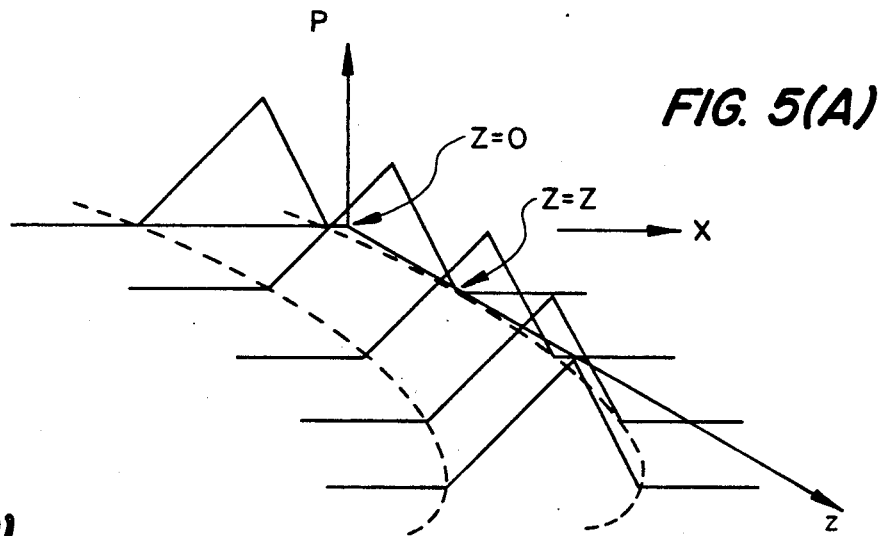
FIGS. 5(A)-5(D) are diagrams illustrating the pressure and phase relationship for a spherical pumping wave onto Z axis of the measuring method at various times.
Figure 5B:
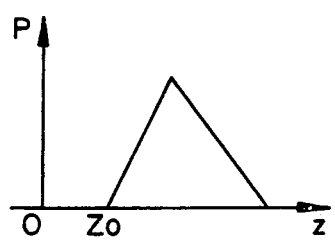
Figure 5C:
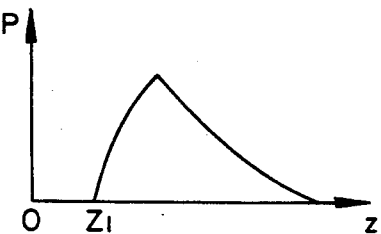
Figure 5D:
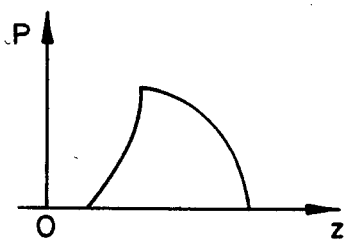

FIG. 5(B) shows the sound pressure distribution of an ideal plane pumping wave, by which a probing wave will be affected while the probing wave propagates on the Z axis. The probing wave propagates from $z=z_0$ (at $t=0$) to $z=z$ (at $t=t$), during that time the pumping wave passes over the Z axis, and affects the probing wave. As can be seen in the figure, the time t or time axis can be replaced by the z or Z axis. FIG. 5(C) shows the sound pressure distribution of a spherical pumping wave on the Z axis, from which the probing wave will be affected, while the probing wave propagates on the Z axis. In the figure, the probing wave was at $z=z_r$ at the instant $t=0$, when the front edge of pumping wave arrived at the Z axis. The deformation of the sound pressure curve, compared with that of (B) will be explained as follows. For the plane pumping wave, sound pressure is uniform on the Z axis, that is it varies only with time. So, if sound pressure P varies in a triangular shape as shown in the FIG. 5(A), the sound pressure which will affect to the probing wave, will be as shown in FIG. 5(B). For a spherical pumping wave, on the other hand, the pumping wave diverges when it propagates, and it decreases in sound energy (pressure). So, sound pressure is the highest at the center of the wave front (at $z=z_r$ in the Figure). As the probing wave propagates from $z_r$, the sound pressure of the pumping wave decreases, and it decreases even more when it passes the edge of the pumping wave. This tendency is enhanced by the sound loss of the medium, because, the portion of the pumping wave apart from the center of the pumping beam must propagate a longer distance to reach to the Z axis, compared with the portion in center part. FIG. 5(D) shows another sound pressure distribution of a spherical pumping wave, which the probing wave will encounter on the Z axis. In this case the probing wave was at $z=0$, when the front edge of pumping wave arrived at the Z axis ($t=0$). Using similar reasoning, it will be understood that the sound pressure varies as shown, contrary to the manner of FIG. 5(C).

Therefore, the weighting function which is equivalent to $g(z)$ in equation (12), and the filter corresponding to $1/G(\omega)$ in equation (15) must have different values along z. So, the characteristics of the filter must be varied at each point on the Z axis to obtain $(B/A)_e(z)$. However, sound pressure which affects the probing wave, at each point on the Z axis, as shown in FIG. 5, can be measured previously. Therefore, the filter characteristics for each value of $z_0$ can be calculated beforehand.

Therefore, it is possible to prepare several of filters, each which are applicable to a specified portion of a specimen to be measured (Z axis). The number of filters to be prepared depends on the resolution and accuracy of the desired measurement. Usually only few filters are enough, because the resolution is also defined by many other factors.

In the actual apparatus the distribution of $B/A(z)$ can be obtained in the same way as that of the plane pumping wave by applying various filters to the output of phase detector 8 in FIG. 3. The output of these filters are switched one by one corresponding to the portion to be measured. It is also possible to design a filter having variable characteristics.

For the filter which sequentially varies its characteristics, a digital filtering technique can be applied to the output of the phase detector after an A/D (analog-digital) conversion.

Another method available to reduce the effect of the spherical pumping wave is to separate the transducer for pumping wave generation as far as possible from the medium to be measured. Using this method the approximation of spherical wave to plane wave becomes better, however, this methods needs a high power pumping wave and as a result, a practical balance between the resolution and the required power is necessary.

Figure 6:
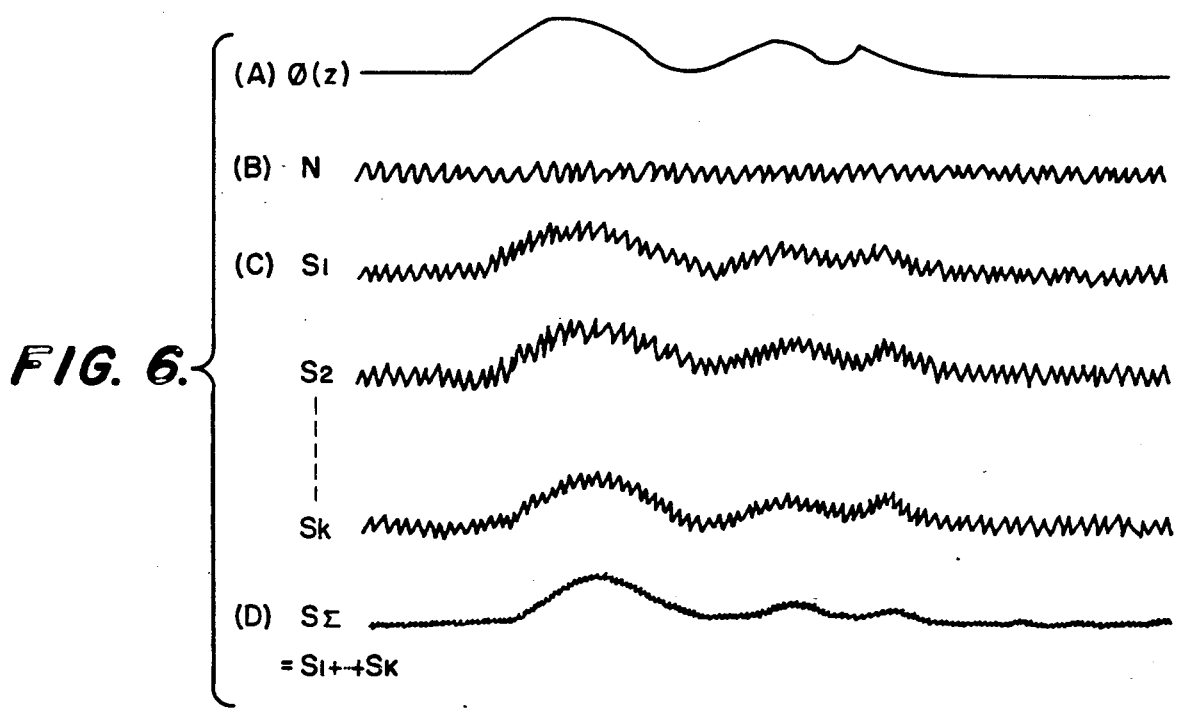
FIG. 6 is a diagram illustrating the waveforms of a signal and noise at an input and an output of the adding circuit of the measuring method according to the present invention having a pumping wave which propagates perpendicular to the probing beam.

Next, a method to increase the S/N (signal to noise) ratio of a measurement will be discussed. When the phase deviation of the probing wave because the equivalent non-linear parameter is small or sound pressure of pumping wave is small, noise produced by the circuits increases so high that detection of the phase deviation $\phi(z)$ is impossible, and $(B/A)_e(z)$ obtained from $\phi(z)$ also includes much noise as shown in FIG. 6. In the FIG. 6, curve (A) shows the output of phase detector (designated 8 in FIG. 3) without noise. Curve (B) indicates schematically a form of noise. Curves (C) show a practical output of the phase detector $\phi(z)$.

To extract the curve (A) from curve (C), an adding circuit is provided which adds the output of the phase detector such as $S_1 \sim S_k$, K times at the same position along the probing beam. As a result, the signal amplitude increases as much as K times, but the noise amplitude increases as much as only $\sqrt{k}$ times, because noise is irregular and added as a power summation. Consequently, S/N ratio of the phase detector output can be improved $\sqrt{K}$ times as shown in FIG. 6(D). This adding circuit is also called a synchronized adding circuit.

FIG. 7 is a block diagram of an apparatus embodying the present invention comprising the above device. In FIG. 7 like reference numerals are used for the same or corresponding parts as in FIG. 3. In the FIG. 7, 12 is the adding circuit which adds the signal of the phase detector output, and 13 is a delay circuit which delays the output signal of the adding circuit 12. Delay circuit 13 delays the output signal of 12 as much as a period T, the repetition time of the pumping pulse. These circuits are well known in the art, and they can be performed on a digital signal by converting the output signal of the phase detector into a digital signal using an A/D converter.

Applying the present invention, it is possible to realize an apparatus to display the distribution of parameter $(B/A)_e$ in two-dimensions or three-dimensions. As mentioned above, the distribution of the parameter can be measured along the probing beam, this is analogous to a line scanning measurement. So, if the transmitting and receiving transducer pair is kept in a fixed relative position, and the pair moves in the X or Y direction, the pair provides a plane scanning, and a two-dimensional display can be obtained. Further, if the couple moves in the X and Y directions, three-dimensional scanning occurs, and a three dimensional display can be provided.

Figure 8:
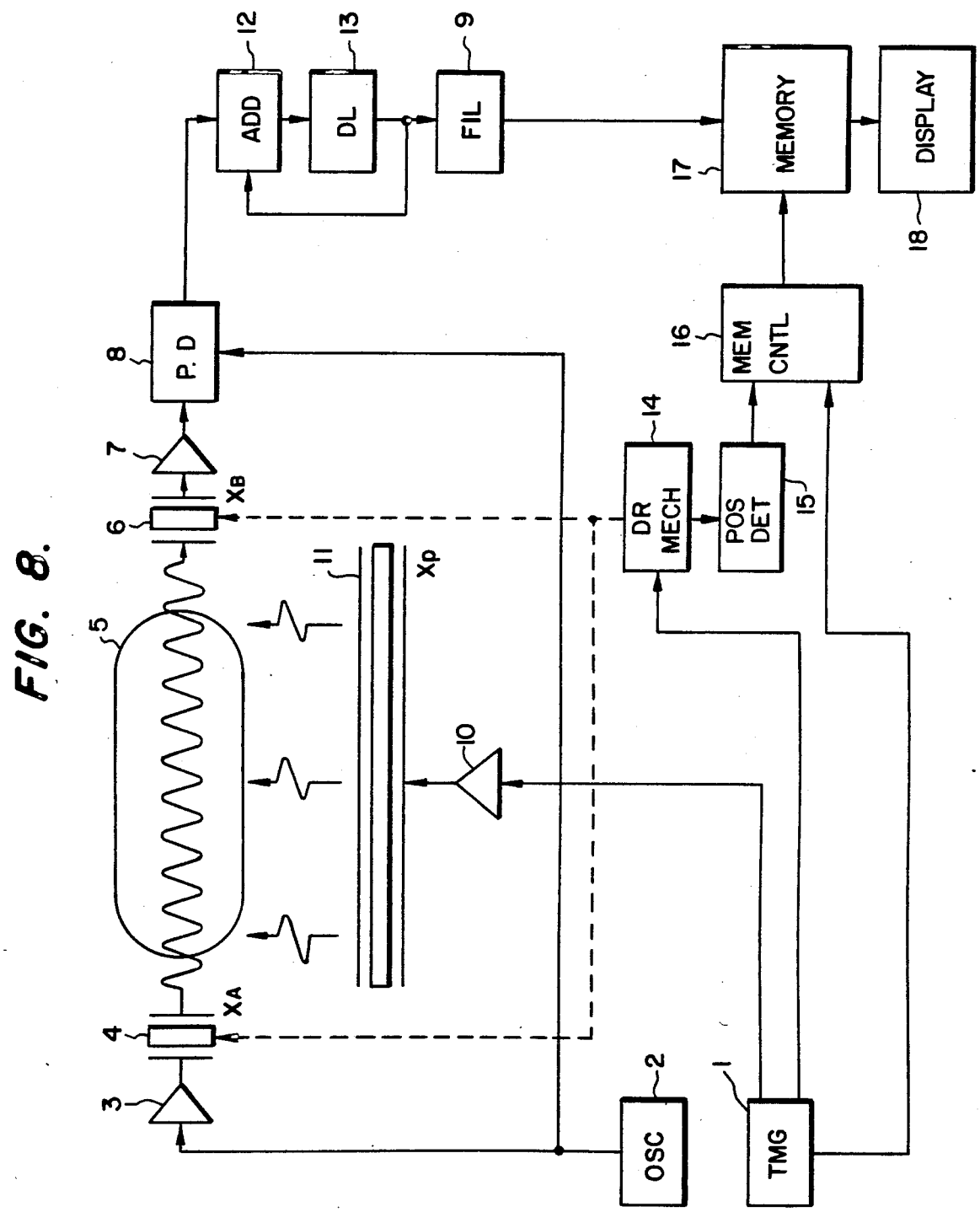
FIG. 8 is still another block diagram of a measuring apparatus embodying the present invention having a pumping wave propagating perpendicular to the probing beam, a scanning mechanism and a display unit to obtain a two or three dimensional distribution of the equivalent non-linear parameter in the acoustic medium.

FIG. 8 shows a block diagram of the apparatus described above. The figure uses like numerals designating like or similar parts as in FIG. 7. In FIG. 8, 14 is a driving mechanical unit which shifts a pair of the transducers 4 and 6 using a device such as a stepping motor driven by a control pulse from timing controller 1. Position detector 15 detects the position of the pair of transducers, using a position finder such as a rotary encoder joined to a shaft of the stepping motor. Memory controller 16 generates the memory address corresponding the output of position detector 15, based on control signals such as a synchronous signal and clock signal for the pumping wave from timing controller 1. Memory 17 stores the measured data for the parameter $(B/A)_e(z)$ after converting an analog signal from filter 9 into a digital signal.

The memory content are processed by control and address signals from write/read from memory controller 16. Display 18 reads the data from memory 17 and displays the distribution of the parameter $(B/A)_e$.

Disclosed above is a first method and its application according to the present invention for measuring an equivalent non-linear acoustic parameter. Many application and modification may occur for the one skilled in the art. For example, the scanning method can be modified to electronic scanning. In this case, there is no need to use the moving mechanism. An afterglow characteristic of a display tube can be applied without using memory 17 for the two-dimension display of $(B/A)_e(z)$. These changes are all within the scope of the present invention.

Next, a second method for measuring the acoustic non-linear parameter will be discussed. This method is a modification of the first method, however, it provides additional merits in a practical application. The significant feature of the second measuring method is the application of the pumping wave along the same axis of the probing beam.

Figure 9:
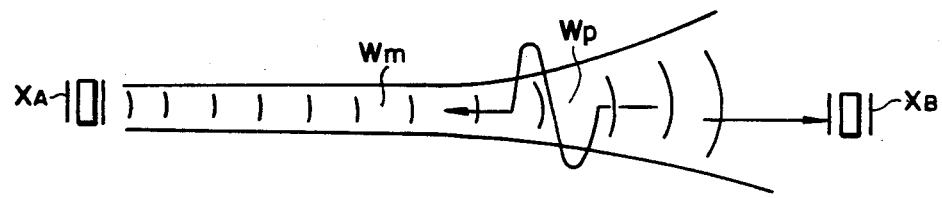
FIG. 9 is a diagram illustrating the principle of the second measuring method of the present invention, having a pumping wave which propagates along the probing beam in a reverse direction.

As explained with respect to the compensation for a spherical pumping wave. It can be understood that, the pumping wave in FIG. 1 is not always necessarily perpendicular to the probing beam. Therefore, as shown in FIG. 9, an axis of the pumping wave is rotated in the counter clockwise by 90° degree, and it travels in the opposite direction to the probing beam. In FIG. 9 the probing beam are shown by $W_m$, and transducers for it is shown as $X_A$ and $X_B$. The probing wave propagates from left to right and the pumping wave $W_p$ propagates from right to left through the probing beam. The transducer generating the pumping wave is not shown in the figure.

Figure 10:
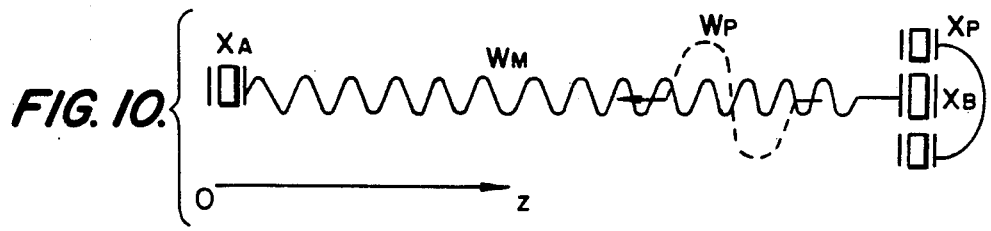
FIG. 10 illustrates a relationship between the pumping wave and the probing wave of the second measuring method.

FIG. 10 shows an arrangement of transducers for the second method. The probing beam and the transducer for the probing wave are the same as those of FIG. 1. A pair of transmitting transducer $X_A$ and a receiving transducer $X_B$ are used, but the pumping transducer $X_P$ is placed around $X_B$ as shown in FIG. 10. The pumping wave $W_P$ is shown with a broken line since it propagates along the probing wave beam, but in the opposite direction to the probing wave $W_p$.

Distribution of the conventionally defined non-linear parameter can be obtained in a way quite similar to the way described previously. The wave train of the probing wave (a continuous wave) is stamped on a phase change by a pulse of the pumping wave. The stamped information is detected by the phase detector, and the information related to the non-linear acoustic parameter is extracted from it.

Figure 11A:
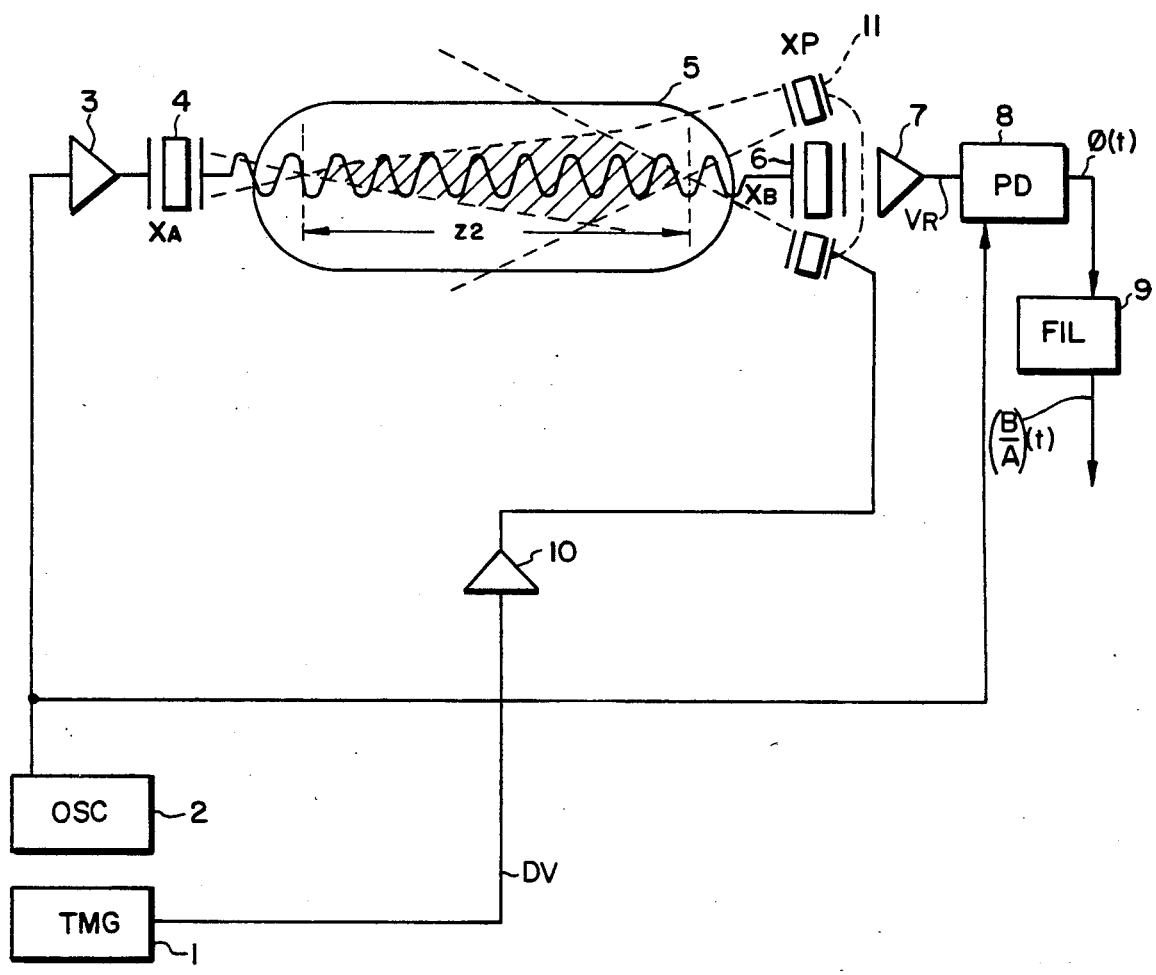
FIG. 11(A) is a block diagram of the measuring apparatus of the second measuring method.
Figure 11B:
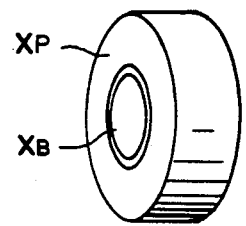
FIG. 11(B) and FIG. 11(C) are a perspective view and a cut-away view of a transducer, combining the pumping transducer and the receiving probing transducer for the second measuring method.
Figure 11C:
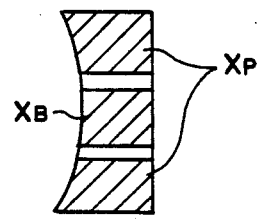

A block diagram for a preferred embodiment of the second measuring method is shown in FIG. 11(A). The figure uses similar reference numerals and symbols for the same or corresponding parts as in FIG. 3. A pumping transducer 11 ($X_P$) is arranged around the receiving transducer $X_B$ for the probing wave. A shadowed portion in medium 5 is a portion in which the non-linear parameter can be measured and its length is indicated by $z_2$. FIG. 11(B) is a diagram illustrating a structure of the transducer 11. $X_B$ is a probing transducer for receiving the probing wave $W_m$. $X_P$ is a pumping transducer shaped as a ring surrounding the receiving transducer $X_B$. FIG. 11(C) shows a cut-away view of the transducer 11 in FIG. 11(B).

In FIG. 11(A), receiving amplifier 7 provides a signal output $V_R$ corresponding to the modulated probing wave, phase detector 8 detects the phase change in $V_R$ and produces an output $\phi(t)$. This output is a train of the phase changes sequentially received, having been stamped with the non-linear parameter (B/A) of the respective position on the probing wave, where the probing wave encountered the pumping wave pulse. As mentioned before, $\phi(t)$ is related to the space distribution of (B/A). The output of filter 9 is proportional to the space distribution of the non-linear parameter (B/A).

In this block diagram, it is simply assumed that the sound pressure waveform does not change during propagation through medium 5, so a characteristic of filter 9 is constant. Usually, in the second method, the wave form of the pumping wave formed on the probing beam does not change as much as in the first method. However, if the waveform of pumping wave changes greatly, it is necessary to compensate in an amount equal to the change. This compensation can be done using several filters designed based on data of for the sound pressure on the Z-axis measured previously without a specimen, in a manner similar to that described with respect to the first measuring method.

Further, if the pumping wave attenuates as it propagates along the acoustic medium without the accompanying distortion of its waveform, it is not necessary to change the filter characteristics with time. Such a case often occurs when measuring a large sample. In such a case, the compensation for the attenuation of the pumping wave can be accomplished rather easily. It can be done by merely varying the amplification of the phase detector output signal ($\phi(t)$) in synchronizim with the pumping wave propagation through the acoustic medium.

Figure 12:
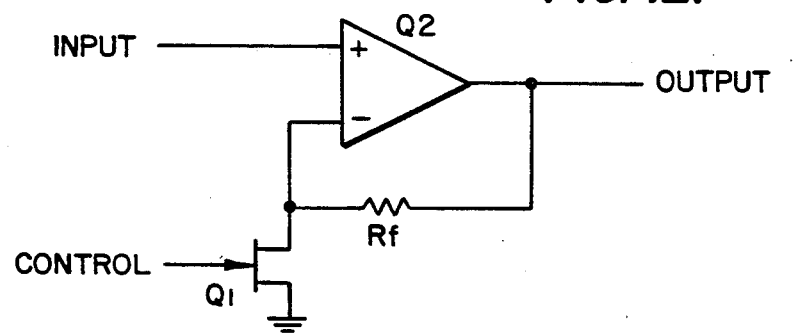
FIG. 12 is a block diagram of a Time Gain Control Amplifier (TGC) provided at the output circuit a phase detector of the measuring apparatus.

This type of amplification control can be done by a "Time Gain Control amplifier" as shown in FIG. 12. Such an amplifier is often used in an ultrasonic echo imaging apparatus, and is well known in the art. In FIG. 12, the amplification factor of operational amplifier $Q_2$ can be varied by a signal produced a field effect transistor (FET) $Q_1$, and where a control signal is applied to the transistor $Q_1$. Closed loop gain of the TGC circuit can be expressed by $$1 + \frac{R_j}{R_{FET}}$$

where, $R_{FET}$ is the equivalent resistance of $Q_1$, and $R_f$ is the resistance of feedback resistor $R_f$ in FIG. 12. Since $R_{FET}$ can be varied by the control signal, the gain is varied in accordance with the control signal. If the control signal is varied with time, the gain is also varied with time.

Figure 13:
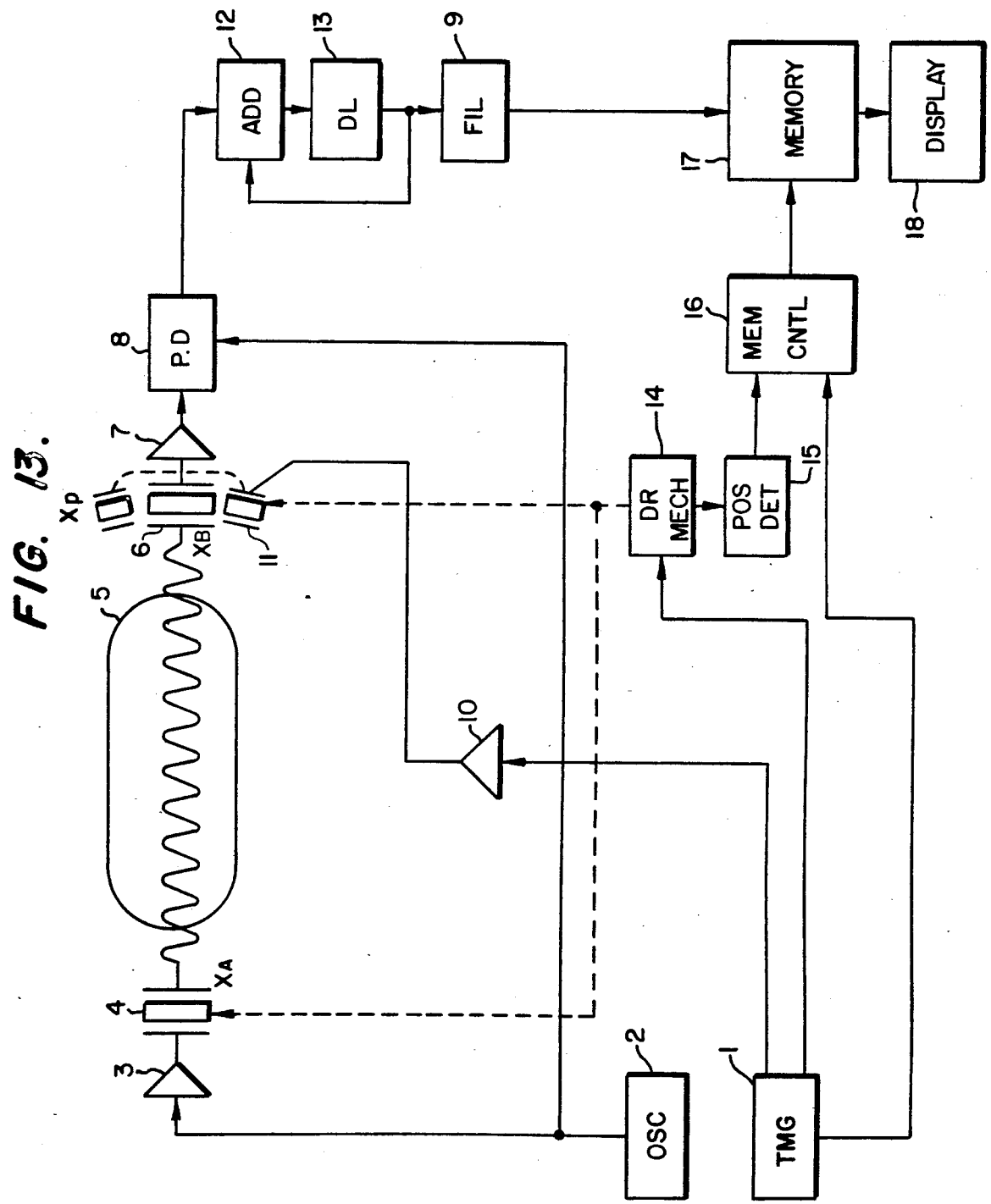
FIG. 13 is a block diagram embodying the measuring apparatus of the second measuring method, comprising a scanning mechanism and a display unit to obtain a two or three dimensional distribution of the equivalent non-linear parameter in the acoustic medium.
Figure 14A:
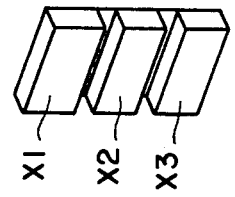
FIGS. 14(A)-14(D) are perspective diagrams of various transducer constructions for the second measuring method of the present invention.
Figure 14B:
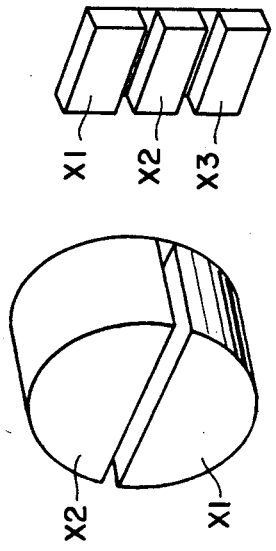
Figure 14C:
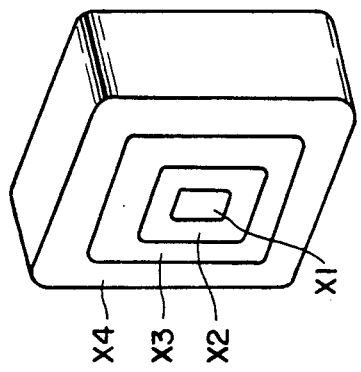
Figure 14D:
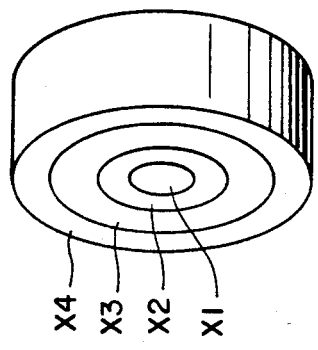

A block diagram of an apparatus embodying the second measuring method is shown in FIG. 13. In the FIG. 13, same reference numerals or symbols designates the same or corresponding parts as in FIG. 8. In comparing FIG. 13 to FIG. 8 the difference is that the pumping wave transducer 11 is arranged around the probing wave transducer $X_B$. Other parts and their operation are all similar to these of FIG. 8. Operation will be easily understood by one skilled in the art, so as further explanation is omitted for the sake of simplicity.

FIG. 14, including 14(A)–14(D) shows some examples of the structure of transducers applicable to the present invention. In the FIG. 14(A) shows a transducer having an annular structure in which $X_1$ is used for receiving the probing wave and $X_2 \sim X_4$ are used for the pumping wave. Focusing the pumping beam is controlled easily by controlling the phase of the driving pulse applied to each of them. The annular structure can be modified as in 14(B). The aperture of the transducer can be modified into a semicircle as shown in 14(C), or a rectangle arrangement as shown in 14(D). In the structure of 14(D), the transducer $X_2$ is used for receiving the probing wave, and $X_1$ and $X_3$ are used for the pumping wave.

Electro-scanning can be applied to the present invention by applying a phased array or linear array technology, which is known in the art. FIGS. 15(A) and 15(B) show the embodiments in which the array type transducer is applied to both receiving the probing wave and transmitting the pumping wave. In the figures, $Y_2$ is used for the probing wave and $Y_1/Y_3$ are for the pumping wave. In FIG. 15(C) or 15(D), $Y_2$ is the array transducer for receiving the probing wave, $Y_4$ or each of $Y_4$ and $Y_5$ is a single plate transducer for the pumping wave. For the scanning method of the array transducer, a so called linear scan or sector scan can be applied. These are well known in the art and they are not important to the spirit of the present invention and further explanation is omitted.

Figure 16A:
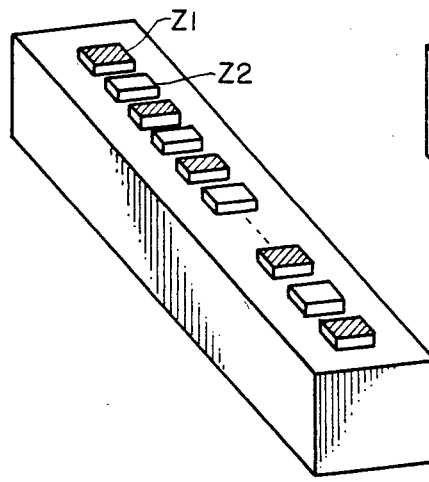
FIGS. 16(A)-16(B) are perspective diagrams of the transducer construction for the pumping wave radiation and probing wave reception using an array transducer, for the second measuring method, where
Figure 16B:
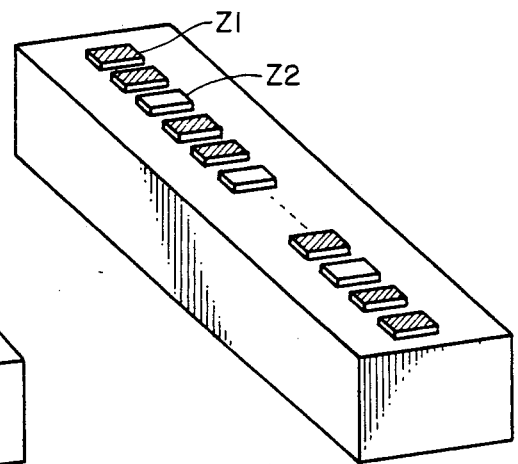

Another example of an array transducer technique that can be applied to the present invention is shown in FIGS. 16(A) and 16(B) where element $Z_1$ is for pumping wave transmission and element $Z_2$ is for probing wave reception. In FIG. 16(A) the elements are arranged alternately, but this alternate arrangement is not always required and the elements can be arranged freely as shown in FIG. 16(B).

Figure 17A:
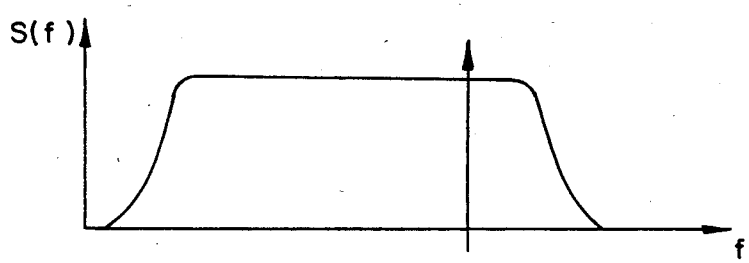
FIG. 17(A) shows a total serviceable sound frequency band of the transducer.
Figure 17B:
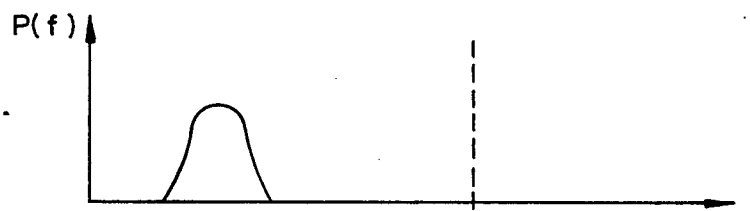
FIG. 17(B) shows a sound frequency band for pumping wave radiation and FIG. 17(C) shows a sound frequency band for probing wave reception.
Figure 17C:
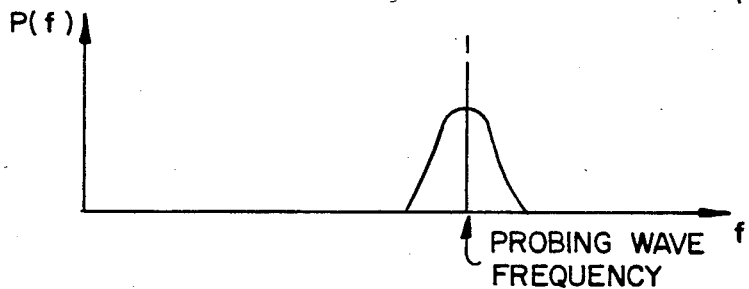

Further more, one transducer element can be used for both receiving the probing wave and transmitting the pumping wave. Such a transducer must have sound frequency characteristics which are sufficiently wide as shown in FIG. 17(A). The transducer is driven so as to radiate the pumping wave in a frequency band as shown in FIG. 17(B), and the receiving amplifier for the probing wave has frequency characteristics as shown in FIG. 17(C). Using such a transducer, the beam of the pumping wave can be automatically collimated with the probing beam because the pumping transducer is placed at the same position as the probing transducer. The array transducer technology and electronic scanning can also employ this method.

Figure 18:
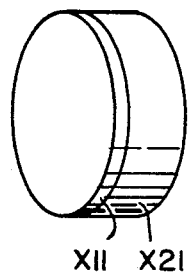
FIG. 18 is a perspective view of a transducer which has a layer structure where the front layer is for the receiving transducer and back layer is for the pumping transducer.

Different effects from the above explanation can be expected when stacking two types of transducers, as shown in FIG. 18. Generally, different materials are used for a transducer, such as PZT (a trade name of CLEVITE Corp., Piezo electric device composed of $P_b(T_iO_3, Z_rO_3)$) and PVDF (an abbreviation of "polyvinylidene fluoride"). PZT is hard material and its acoustic impedance is high as compared with biomedical tissue, while PVDF is soft and its impedance is close to that of biomedical tissue. So, as shown in the figure, the transducer has a piled layer type structure in which PVDF is applied to a front layer $X_{11}$ as the receiving probing transducer, and PZT is used in a back layer $X_{21}$ as the pumping transducer. The front layer $X_{11}$ is a surface to contact an object, so PVDF acts as impedance matching layer for the object such as biomedical tissue. The back layer $X_{21}$ PZT is also suitable for the front layer $X_{11}$ PVDF, because it requires high impedance as a backing for high radiation efficiency.

An array transducer technique also can employ such stacked types of transducers. It is obvious that the array technology described above can employ a measuring apparatus using the front measuring method.

As can be seen from above description, the second measuring method has additional merits as compared with the first method, that is: a more compact apparatus can be assembled; the temperature measurement performed can be more sensitive; and the pumping transducer can be made more easily. Therefore, it can be said that the second method is easier than the first method in handling and practically.

Next, as an example of the application of the present invention, a temperature measuring system to measure the internal temperature of an acoustic medium will be disclosed. The fundamental principle of the temperature measurement is as follows. The value of (B/A) or its distribution will vary with temperature. So, if these values are measured and stored beforehand from a sample, it is possible to know the temperature of the object being measured.

Figure 21:
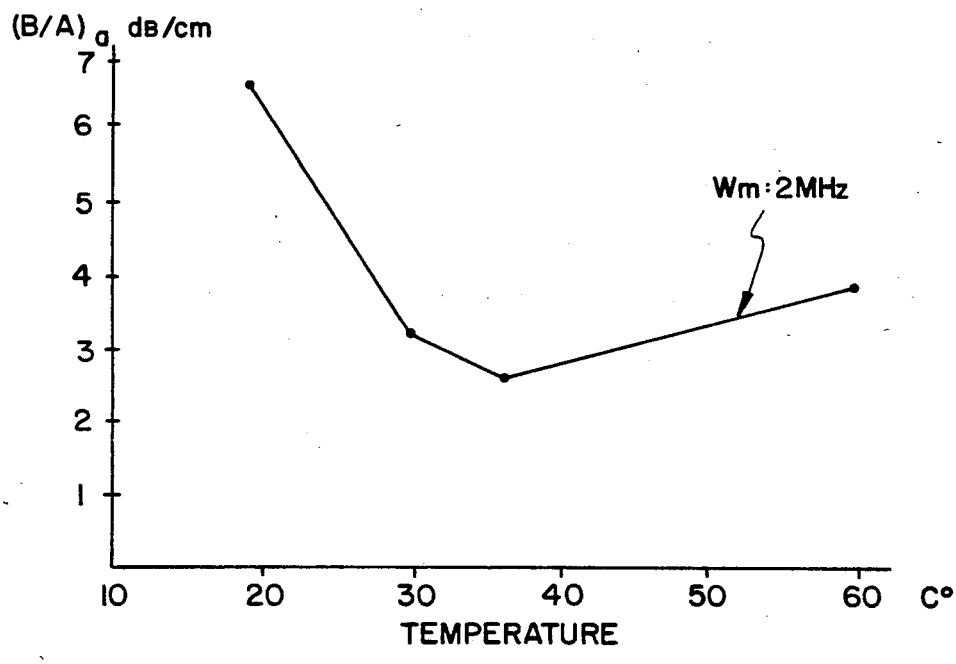
FIG. 21 shows a conversion curve between apparent $(B/A)_a$ and $\Delta T$, contained in unit 20 of the block diagram of FIG. 19.

FIG. 21 shows an example supporting above considerations. The curve in the figure shows relationship of (B/A) to the temperature. This curve was obtained from measurement of fresh meat, varying the temperature of the meat, and measuring same with a probing wave frequency of 2 MHz. When such a curve is known beforehand for various samples, it is possible to know the temperature of the sample from the value of (B/A).

The non-linear parameter (B/A) (z) mentioned above was derived assuming that sound speed $C_0$ and density $\rho_0$ are constant during the phase change, representing the second term of equation (1). However, if not only the parameter (B/A) but also $C_0$ and/or $\rho_0$ vary locally in the acoustic medium, the phase change should be expressed strictly by the following function, f:

$$f\{(B/A), C, \rho\}(z) = \frac{1}{\rho_0 C_0} \left(\frac{B}{A}\right)(z). \quad (20)$$

When the temperature of the acoustic medium varies, the value of $\rho_0$, $C_0$, and (B/A) also vary. Therefore, the temperature variation can be obtained from measured data for the function f.

Usually, it can be assumed that density $\rho_0$ does not depend on temperature very much but $C_0$ and (B/A) vary in accordance with the temperature variation. Therefore, if the temperature of the acoustic medium varies from $T_0$ to $T_1$, the following equation can be obtained:

$$\Delta f = \left\{\frac{1}{\rho_0 C_0}\left(\frac{B}{A}\right)\right\}(z)_{T_0} - \left\{\frac{1}{\rho_0 C_0}\left(\frac{B}{A}\right)\right\}(z)_{T_1} \quad (21)$$

$$\approx \left\{\frac{1}{\rho_0 C_0}\left(\frac{B}{A}\right)\right\}(z)_{T_0}$$

$$\left\{\frac{\beta}{\left(\frac{B}{A}\right)(z)_{T_0}} - \frac{\alpha}{C_0(z)_{T_0}}\right\} \Delta T.$$

where, $\Delta T = T_1 - T_0$, $\alpha$ and $\beta$ are constant. The difference in the value of the function f before and after the acoustic medium has changed temperature can be derived as follows (where, $\Delta$ shows the difference)

$$\rho_0(z)_{T_1} = \rho_0(z)_{T_0} = \rho_0(z),$$

$$C_0(z)_{T_1} = C_0(z)_{T_0} + \alpha \Delta T,$$

$$(B/A)(z)_{T_1} = (B/A)(z)_{T_0} + \beta \Delta T.$$

In equation (21), $\Delta f$ can be measured by the present invention which is for measuring an apparent non-linear parameter of the acoustic medium, so if $\alpha$, $\beta$, $C_0(z)_{T_0}$, $\rho_0(z)$, and $(B/A)(z)_{T_0}$ are given, $\Delta T$ can be derived from this equation. These parameters can be obtained by actual measurement, except $(B/A)(z)_{T_0}$. The parameter $(B/A)(z)_{T_0}$ can be derived because the first term of the above equation (21) can be measured and $\rho_0(z)$ and $C_0(z)_{T_0}$ are given.

Figure 19:
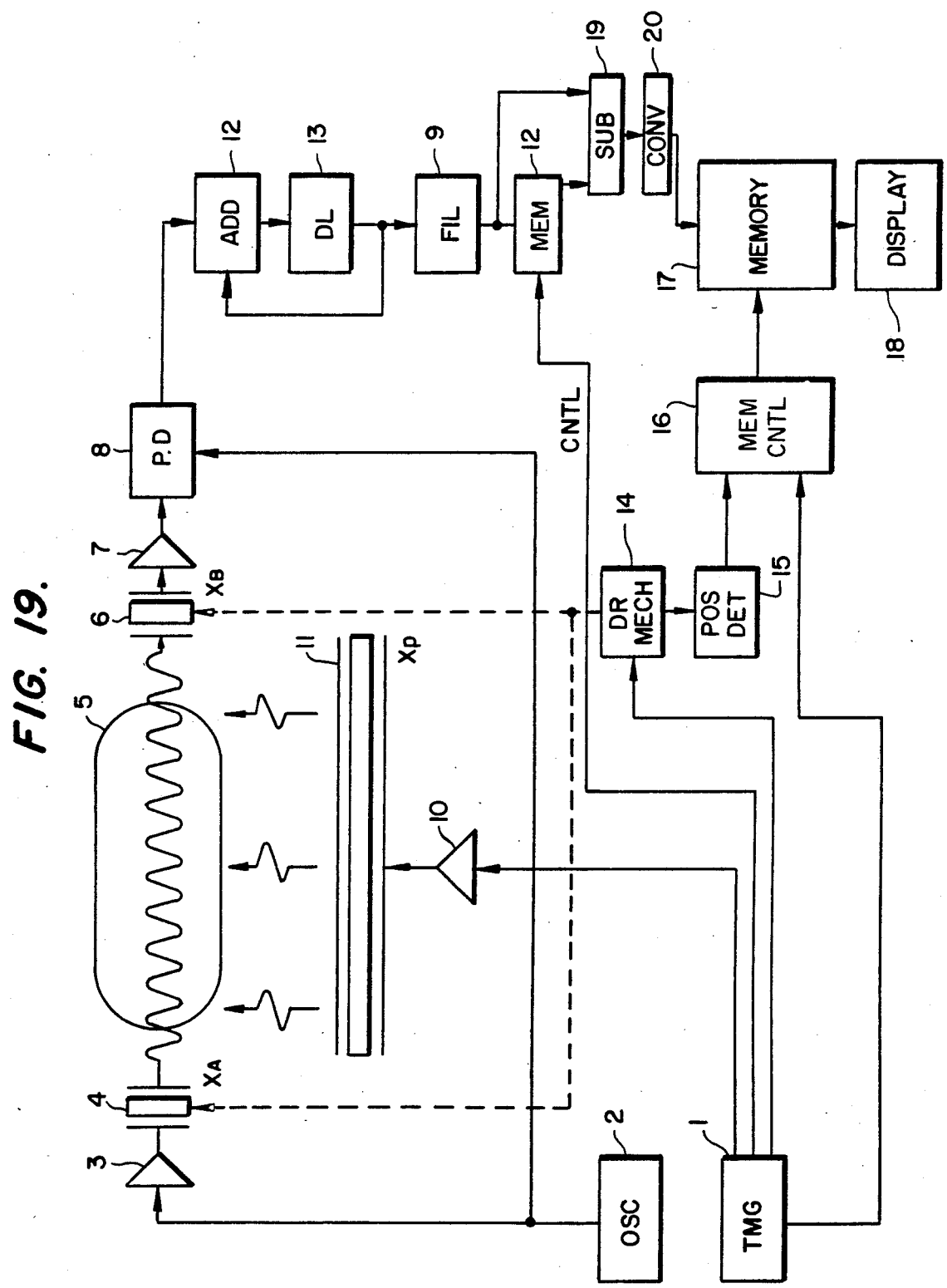
FIG. 19 is a block diagram of the temperature measuring system, which is an embodiment of the apparatus of the present invention.

FIG. 19 shows a block diagram of an apparatus for measuring the internal temperature of the acoustic medium noninvasively. It is an example of the present invention, and the inventors believe that this is the first method which made it possible to measure the internal temperature of an acoustic medium, such as a human body for example, without actually reaching to the measuring point.

In FIG. 19, the same reference numerals or symbols designate the same or similar parts as in foregoing FIG. 8 or 13, and function of each corresponding part is also similar. The pumping wave in the figure intersects perpendicularly with the probing beam as in the case of FIG. 8 (the first method). The second method shown in FIG. 13 that uses the pumping wave which propagates along the probing wave in a reverse direction is also applicable.

The block diagram of FIG. 19 therefore comprises the same units described with respect to FIG. 8, but the following functions and units are added for the temperature measuring apparatus. A memory unit 12 memorizes the values of the function f before the acoustic medium is changed in temperature. A subtractor 19 provides a difference between the function f memorized in memory unit 12 and the value of the newly measured f. Then, $\Delta f$, the difference in the value of function f before and after a temperature change in the acoustic medium is obtained.

Figure 20:
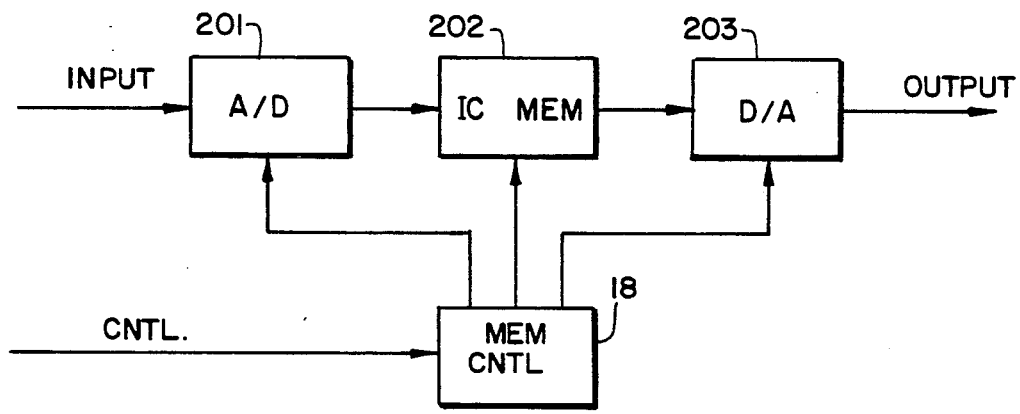
FIG. 20 shows a block diagram of a memory unit 12, used in the circuit of FIG. 19.

FIG. 20 shows an embodiment of memory unit 12. Where, 201 is an analog-to-digital converter, 203 is a digital-to-analog converter, and 202 is an integrated circuit memory. The memory unit is controlled using a controller 18 synchronized with the pumping wave transmission.

In this manner, the value of $\Delta f$ in equation (21) can be measured. Therefore $\Delta T$, the temperature difference can be derived by conversion circuit 20, containing the relation between $\Delta f$ and $\Delta t$, obtained experimentally in advance. Such a relationship is usually nonlinear as shown in FIG. 21. The unit 20 can be realized with a memory containing a conversion table.

FIG. 21 shows an example of data measured by the above disclosed apparatus. A piece of fresh beef was used as the material of the acoustic medium. Measurement was made as follows: a measuring point in materials was selected optionally; the temperature was varied experimentally measuring its temperaure by a minute sensor in a range from 10° C. to 60° C.; the phase change, namely f was measured as apparent the non-linear parameter $(B/A)_a$ using constant $C_0$ and $\rho_0$ at room temperature; and frequency of the probing wave was set 2 MHz. In FIG. 21, the ordinate axis coordinate value is the parameter $(B/A)_a$, and the abscissa axis coordinate value is internal temperature at a designated point in the acoustic medium. The inventors believe this is the first noninvasive temperature data measured, which was impossible in the prior art. As mentioned before, such a noninvasive measurement became possible without actually reaching the measuring point. When such data is accumulated for many kinds of medium, including human body, extensive applications such as hyperthermia cancer therapy is possible.

We claim:

1. A measuring method for a non-linear parameter of an acoustic medium comprising the steps of:
   (A) projecting a probing beam as a probing wave which is a continuous ultrasonic wave propagating through said acoustic medium;
   (B) projecting a pumping wave which is an ultrasonic pulse wave propagating through said acoustic medium to interact with said probing wave;
   (C) detecting a phase change in said probing wave which is caused by said pumping wave; and
   (D) determining the non-linear parameter of said acoustic medium from said phase change by deconvolution.

2. A measuring method for a non-linear parameter of an acoustic medium according to claim 1, wherein said pumping wave intersects said probing beam.

3. A measuring method for a non-linear parameter of an acoustic medium according to claim 1, wherein said probing beam has a first direction of projection and said pumping wave is projected in a second direction along said probing beam opposite to the first direction.

4. A measuring method for a non-linear parameter of an acoustic medium according to claim 1, wherein step (D) comprises the steps of:
   (D1) measuring the phase change of said probing wave as a function position in said acoustic medium; and
   (D2) deriving a space distribution of the non-linear parameter by filtering said measured phase change using a filter having approximately an inverse frequency characteristic when compared with said pumping wave spectrum.

5. A measuring method for a non-linear parameter of an acoustic medium according to claim 1, further comprising:
   (E) compensating for a deviation in the measured value of the phase change caused by a non-uniform space distribution in said pumping wave, said step (E) comprising the steps of:
   (E1) measuring said space distribution of said pumping wave as a function of position along said probing beam and as a function of time; and
   (E2) varying characteristics of a filter corresponding said measured space distribution value where said filter is in the measurement signal path.

6. An apparatus for measuring a non-linear parameter of an acoustic medium, said apparatus comprising:
   first means for projecting a probing beam which is a continuous ultrasonic wave, propagating through said acoustic medium;
   second means for projecting a pumping wave which is an ultrasonic pulse wave, propagating through said acoustic medium to interact with said probing wave;
   third means for detecting a phase change in said probing wave; by deconvolution; and
   fourth means for producing a distribution of said non-linear parameter from said phase change.

7. An apparatus according to claim 6, wherein said first means comprises:
   first and the second ultrasonic transducers positioned on and contacting opposite sides of said acoustic medium, where said first transducer radiates said probing wave having a power level lower than that of said pumping wave, and said second transducer receives said probing wave propagated through said acoustic medium.

8. An apparatus according to claim 6, wherein said second means comprises a third ultrasonic transducer which radiates said pumping wave having a shaped pumping wave beam whose beam width is wide enough to cover a localized region to be measured in said acoustic medium.

9. An apparatus according to claim 8, wherein said third transducer is positioned to radiate said pumping wave in a direction to intersect said probing beam.

10. An apparatus according to claim 8, wherein said probing beam is projected in a first direction and said third transducer is positioned to radiate said pumping wave in a second direction along said probing beam opposite the first direction.

11. An apparatus according to claim 10, further comprising compensation means for compensating for a deviation in the measured value caused by a non-uniform space distribution of said pumping wave, said compensating means comprising at least one time invariant filter.

12. An apparatus according to claim 11, further comprising variable amplifying means for varying a gain with respect to time corresponding to the propagation of said pumping wave in said acoustic medium.

13. An apparatus according to claim 10, further comprising means for improving a S/N ratio comprising synchronous adding means for summing a plurality of measured values of said phase change at the same position synchronized to said pumping wave pulse.

14. An apparatus according to claim 10, further comprising means for scanning said probing beam to provide one of a two and three dimensional distribution image of said non-linear parameter.

15. An apparatus according to claim 14, wherein said scanning is performed mechanically, moving at least said first and second transducers as a pair relative to said acoustic medium.

16. An apparatus according to claim 14, wherein said scanning is performed electronically using an array.

17. An apparatus according to claim 10, wherein said third transducer has an annular structure and is positioned around said second transducer.

18. An apparatus according to claim 10, wherein said second and third transducers each have a semicircular face arranged in the same circle.

19. An apparatus according to claim 10, wherein said second and third transducers have a rectangular shape, and said third transducer is located adjacent said second transducer.

20. An apparatus according to claim 10, wherein said second transducer and said third transducer comprise a single transducer element having frequency transmission and reception characteristics sufficient to cover both receiving said probing wave and transmitting said pumping wave.

21. An apparatus according to claim 10, wherein said second and said third transducer comprise a layer type transducer, having a front layer as said second transducer, and a back layer as said third transducer.

22. An apparatus according to claim 6, wherein said third means comprises:
  phase detecting means for detecting said phase change of said probing wave and producing a time sequential train signal as an output signal; and
  filter means, having a frequency characteristics approximately inverse to that of said pumping wave, for receiving the output signal from said phase detecting means, and providing a spatially de-convoluted signal representing a localized space distribution of said non-linear parameter.

23. A temperature measuring apparatus for measuring temperature or temperature distribution in a sample without touching the measuring point, said apparatus comprising:
  first means for projecting a probing beam which is a continuous ultrasonic wave, propagating through said sample;
  second means for projecting a pumping wave which is an ultrasonic pulse wave, propagating through said sample to interact with said probing wave;
  third means for detecting a phase change in said probing wave and determining a nonlinear parameter of said sample from said phase change by deconvolution;
  memory means for storing a measured value of said non-linear parameter;
  means for deriving a difference in the measured value due to a change in the temperature of said sample; and
  means for converting said non-linear parameter difference to a temperature change.

24. A temperature measuring apparatus as set forth in claim 23, further comprising means for deriving and storing a space distribution of said temperature change along a path of said probing wave which has propagated through said sample.

25. A temperature measuring apparatus as set forth in claim 23 further comprising scanning and displaying means for providing an image of said temperature distribution in said sample.

26. An ultrasonic acoustic measuring method, comprising the steps of:
  (a) transmitting a continuous probing beam and a pulsed pumping wave through a medium such that the pumping wave interacts with the probing beam;
  (b) detecting phase changes in the probing beam; and
  (c) converting the phase changes into non-linear parameter measurements by deconvolution which provide information relative to the characteristice of the medium.

27. A method according to claim 26, wherein the parameter measured is temperature.

28. An apparatus according to claim 27, wherein the parameter measured is temperature.

29. An ultrasonic acoustic measuring apparatus, comprising:
  transmitting means for transmitting a continuous probing beam and a pulsed pumping beam through a medium such that the pumping wave interacts with the probing beam;
  phase detection means for detecting phase changes in the probing beam; and
  converting means for converting the phase changes into non-linear parameter measurements by deconvolution which provide information relative to the characteristics of the medium.

* * * * *

UNITED STATES PATENT AND TRADEMARK OFFICE
CERTIFICATE OF CORRECTION

PATENT NO. : 4,566,460

DATED : JANUARY 28, 1986

INVENTOR(S) : TAKUSO SATO ET AL.

Page 1 of 5

It is certified that error appears in the above-identified patent and that said Letters Patent is hereby corrected as shown below:

```
FRONT PAGE, [57] ABSTRACT
            line 11, "projects" should be --provides--;
            line 12, "vides" should be --jects--.

FIG. 5(A), "Z=Z" should be --Z=Z_r--.

Col. 1, line 3, after "OF" insert --AN--;

line 68, after "resulting" insert --in a--.

Col. 3, line 3, change "though" to --through--;
        line 5, "received" should be --required--;
        line 21, (line numbering off) "of" should be --or--;
        line 24, "providing" should be --provide--;
        line 35, "frequency" should be --frequencies--.

Col. 4, line 18, "onto" should be --on the--;
        line 49, after "circuit" insert --of--.

Col. 6, line 49, "Detail" should be --Details--;
        line 67, after "receive" insert --the--.

Col. 7, line 41, after "substituting" insert --the--;
        line 57, after "is" insert --the--;
        line 58, after "(13)," insert --the--.
```

UNITED STATES PATENT AND TRADEMARK OFFICE
CERTIFICATE OF CORRECTION

PATENT NO. : 4,566,460

DATED : JANUARY 28, 1986

INVENTOR(S) : TAKUSO SATO ET AL.

It is certified that error appears in the above-identified patent and that said Letters Patent is hereby corrected as shown below:

```
Col. 8, line 1, after "(14)," insert --the--;
        line 65, "(t)" should be --ø(t)--.

Col. 9, line 7, delete "construction an";

line 21, after "of" insert --the--;
        line 65, after "pumping" insert --wave--.
```

THE LINE NUMBERING IN COLUMN 10 IS IN ERROR. THE FOLLOWING CORRECTIONS APPLY TO CORRECT LINE NUMBERING.

```
Col. 10, line 13, after "of" insert --the--;
         line 17, after "is" (second occurrence) insert
                  --,--;
         line 20, delete "to";
         line 36, after "of" insert --the--;
         line 50, delete "of";
         line 51, after "each" insert --of--;
         line 54, after "only" insert --a--.

Col. 11, line 6, "methods" should be --method--;
         line 67, after "sponding" insert --to--.

Col. 12, line 5, "content" should be --contents--;
         line 32, delete "degree";
         line 34, "are" should be --is--;
         line 35, "is" should be --are--.
```

UNITED STATES PATENT AND TRADEMARK OFFICE
CERTIFICATE OF CORRECTION

PATENT NO. : 4,566,460

DATED : JANUARY 28, 1986

INVENTOR(S) : TAKUSO SATO ET AL.

It is certified that error appears in the above-identified patent and that said Letters Patent is hereby corrected as shown below:

```
Col. 13, line 24, delete "of";
        line 36, "synchronizim" should be --synchronism--;
        line 44, before "a" insert --by--;
        line 66, "these" should be --those--;
        line 67, "as" should be --a--.

Col. 14, line 1, after "(D)" insert --,--;
        line 3, delete "In the";
        line 38, "Further more" should be --Furthermore--.

Col. 15, line 15, "practically" should be --practicality--;
        line 19, begin a new paragraph with "The
                  fundamental";
        lines 25-26, [should be joined to make one
                  paragraph].

line 60, equation (21), please delete the equation,
                  the correct equation is as follows:
```

$$--\rho_0(z)_{T1} = \rho_0(z)_{T0} = \rho_0(z),$$

$$C_0(z)_{T1} = C_0(z)_{T0} + \alpha \Delta T,$$

$$(B/A)(z)_{T1} = (B/A)(z)_{T0} + \beta \Delta T,--.$$

```
Col. 16, delete lines 1-6;
        line 10, after "temperature" insert --and--;
```

UNITED STATES PATENT AND TRADEMARK OFFICE
CERTIFICATE OF CORRECTION

PATENT NO. : 4,566,460
DATED : JANUARY 28, 1986  Page 4 of 5
INVENTOR(S) : TAKUSO SATO ET AL.

It is certified that error appears in the above-identified patent and that said Letters Patent is hereby corrected as shown below:

Col. 16, delete lines 13-17, and in place thereof, insert the correct equation:

$$--\Delta f = \left\{\frac{1}{\rho_0 C_0}\left(\frac{B}{A}\right)\right\}(z)_{T0} - \left\{\frac{1}{\rho_0 C_0}\left(\frac{B}{A}\right)\right\}(z)_{T1}$$

$$\simeq \left\{\frac{1}{\rho_0 C_0}\left(\frac{B}{A}\right)\right\}(z)_{T0}$$

$$\left\{\frac{\beta}{\left(\frac{B}{A}\right)(z)_{T0}} - \frac{\alpha}{C_0(z)_{T0}}\right\}\Delta T \quad (21).--;$$

UNITED STATES PATENT AND TRADEMARK OFFICE
CERTIFICATE OF CORRECTION

PATENT NO. : 4,566,460
DATED : JANUARY 28, 1986
INVENTOR(S) : TAKUSO SATO ET AL.

It is certified that error appears in the above-identified patent and that said Letters Patent is hereby corrected as shown below:

NOTE THE NUMBERING OF LINES IN COLUMN 16 IS OFF AND THE FOLLOWING APPLY TO CORRECT LINE NUMBERING.

Col. 16, lines 20, 21, 23, 24, 26, "$t_0$" should be --$T_0$--;

line 59, "circuit memory" should be --memory circuit--.

Col. 18, line 11, "wave;" should be --wave--.

Col. 19, line 21, "a frequency characteristics" should be --frequency characteristics--.

Col. 20, line 24, "characteristice" should be --characteristics--.

Signed and Sealed this

Sixteenth Day of September 1986

[SEAL]

Attest:

DONALD J. QUIGG

Attesting Officer

Commissioner of Patents and Trademarks